(12) United States Patent  
Vesely

(10) Patent No.: US 6,530,952 B2
(45) Date of Patent: Mar. 11, 2003

(54) BIOPROSTHETIC CARDIOVASCULAR VALVE SYSTEM

(75) Inventor: Ivan Vesely, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/745,240

(22) Filed: Dec. 21, 2000

(65) Prior Publication Data

US 2001/0002445 A1 May 31, 2001

Related U.S. Application Data

(63) Continuation-in-part of application No. 09/597,918, filed on Jun. 19, 2000, which is a continuation of application No. PCT/US98/27481, filed on Dec. 23, 1998.
(60) Provisional application No. 60/068,711, filed on Dec. 29, 1997.

(51) Int. Cl.[7] ............................... A61F 2/24; A61F 2/06
(52) U.S. Cl. ...................... 623/2.18; 623/1.24; 623/1.26
(58) Field of Search ................................ 623/2.18, 2.1, 623/2.11, 2.14, 2.12, 1.24, 1.25, 1.26

(56) References Cited

U.S. PATENT DOCUMENTS

| | | | |
|---|---|---|---|
| 3,898,701 A | 8/1975 | La Russa .................... 3/1.5 |
| 4,056,854 A | 11/1977 | Boretos et al. ............... 3/1.5 |
| 4,506,394 A | 3/1985 | Bedard ....................... 3/1.5 |
| 4,680,031 A | 7/1987 | Alonso ....................... 623/2 |
| 4,790,843 A | 12/1988 | Carpentier et al. ............. 623/2 |
| 5,312,360 A | 5/1994 | Behl .......................... 604/164 |
| 5,411,552 A | * 5/1995 | Andersen et al. .............. 623/2 |
| 5,545,214 A | * 8/1996 | Stevens ....................... 623/2 |
| 5,554,185 A | 9/1996 | Block et al. .................. 623/2 |
| 5,571,174 A | 11/1996 | Love et al. ................... 623/2 |
| 5,593,424 A | 1/1997 | Northrup III ................. 606/232 |
| 5,607,446 A | 3/1997 | Beehler et al. ............... 606/198 |
| 5,662,676 A | 9/1997 | Koninckx ..................... 606/198 |
| 5,718,725 A | 2/1998 | Sterman et al. ............... 623/2 |
| 5,807,405 A | 9/1998 | Vanney et al. ................ 623/112 |
| 5,843,181 A | 12/1998 | Jaffe et al. .................. 623/2 |
| 5,855,601 A | 1/1999 | Bessler et al. ................ 623/2 |
| 5,910,170 A | 6/1999 | Reimink et al. ............... 623/2 |
| 5,957,949 A | 9/1999 | Leonhardt et al. ............. 606/194 |
| 6,106,550 A | 8/2000 | Magovern et al. ............. 623/2.38 |
| 6,168,614 B1 | 1/2001 | Andersen et al. .............. 623/1 |
| 6,197,054 B1 | 3/2001 | Hamblin, Jr. et al. .......... 623/2.38 |
| 6,312,465 B1 | 11/2001 | Griffin et al. ................ 623/2.38 |

FOREIGN PATENT DOCUMENTS

WO  99/33414  7/1999

* cited by examiner

Primary Examiner—Corrine McDermott
Assistant Examiner—Alvin Stewart
(74) Attorney, Agent, or Firm—Michael A. Jaffe

(57) ABSTRACT

A cardiovascular valve system including a permanent base unit that is affixed to the patient using conventional sutures or staples, and a collapsible valve having a collapsible frame that mates with the permanent base unit, and supports valve leaflets. An installed collapsible frame may be re-collapsed and disengaged from the permanent housing. A new collapsible valve is then installed, to resume the function of the prosthesis.

20 Claims, 24 Drawing Sheets

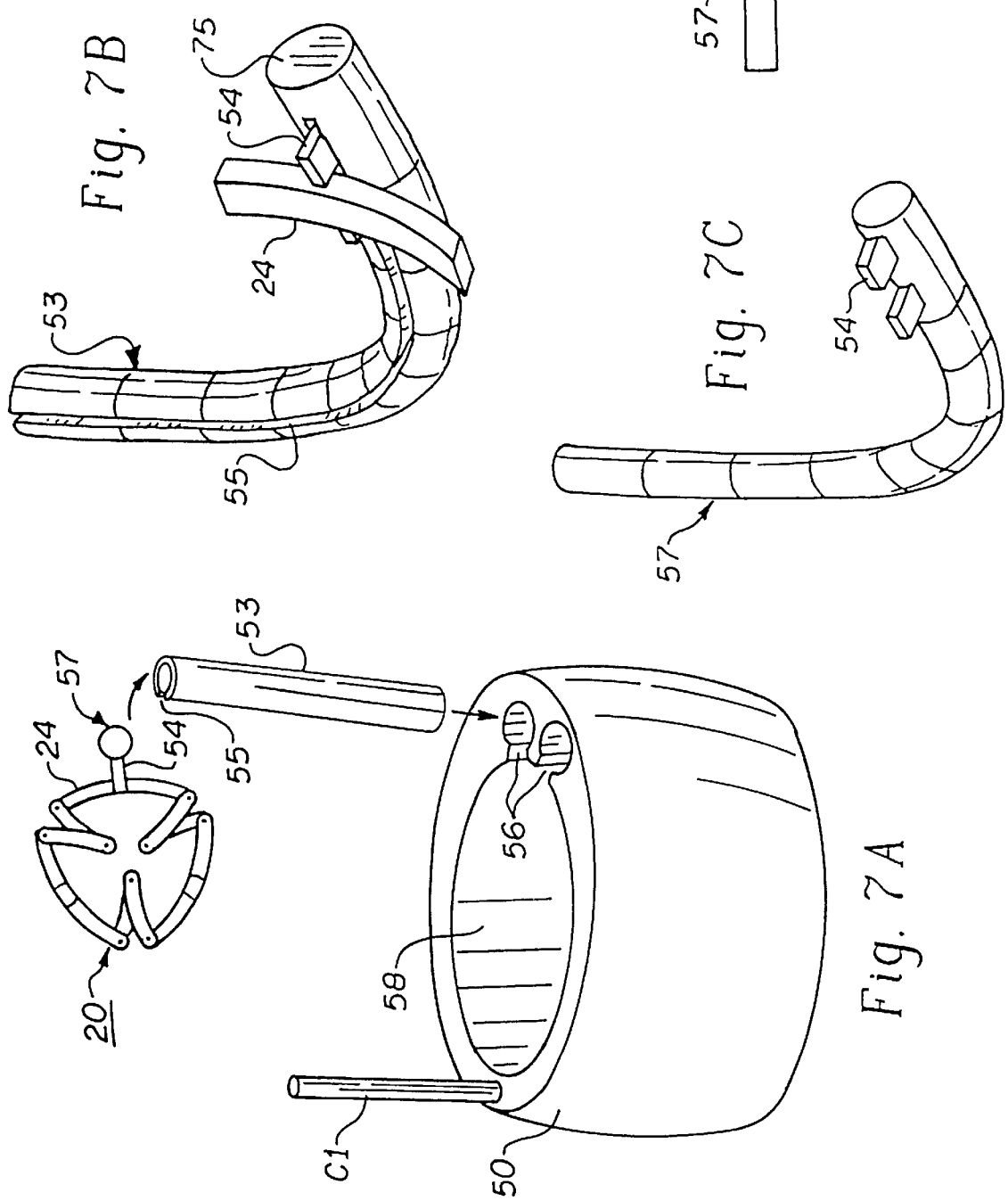

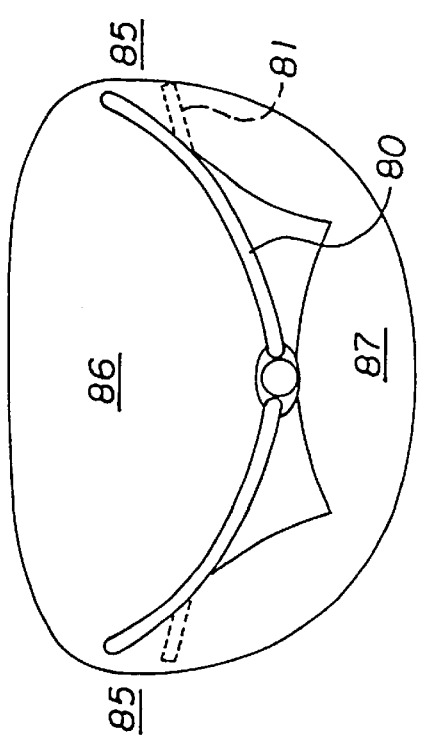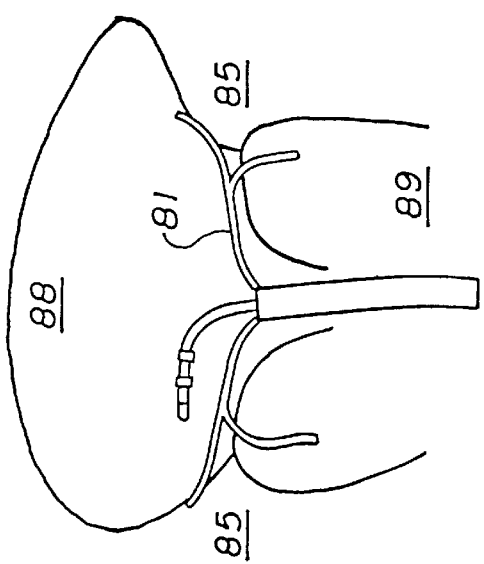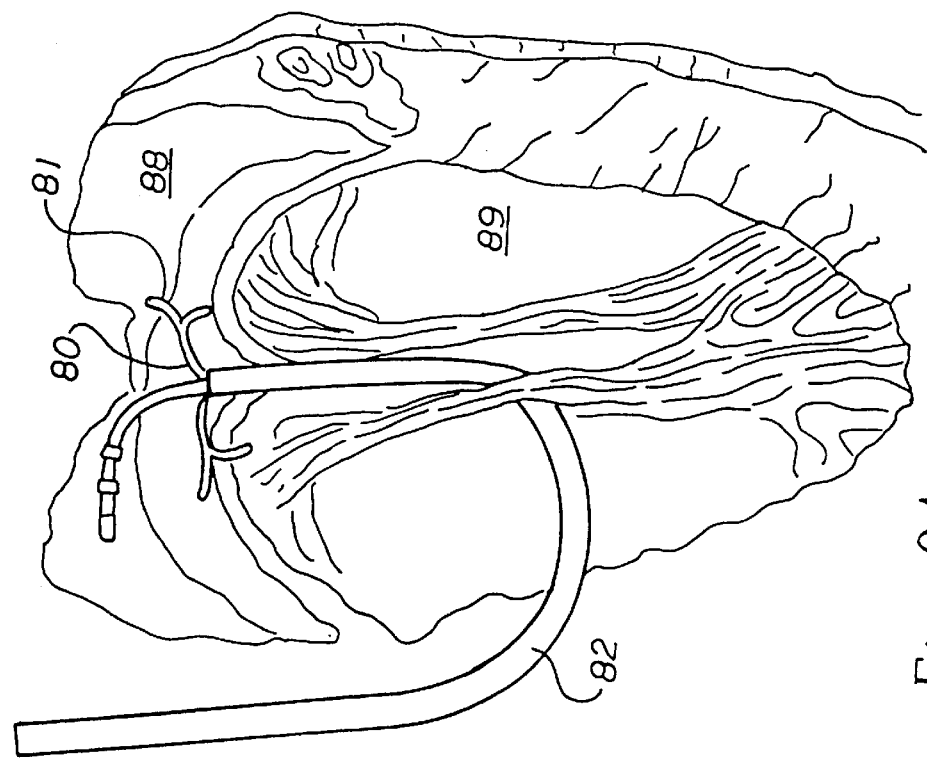

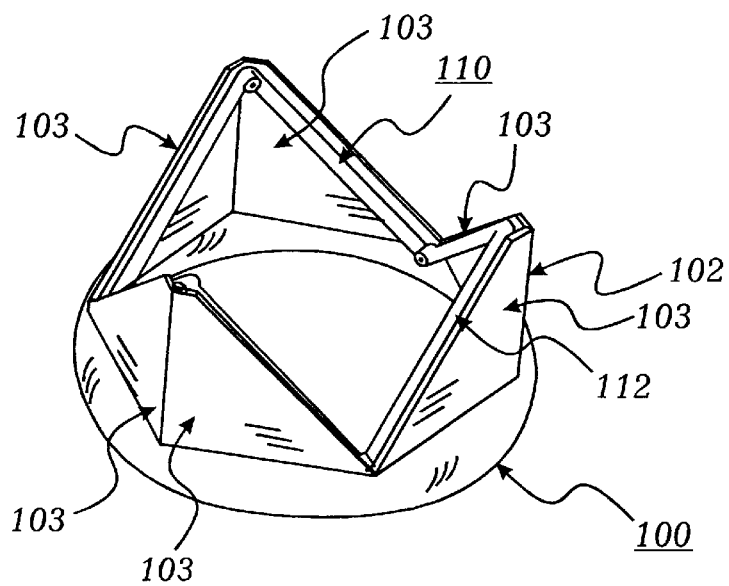
Fig. 15
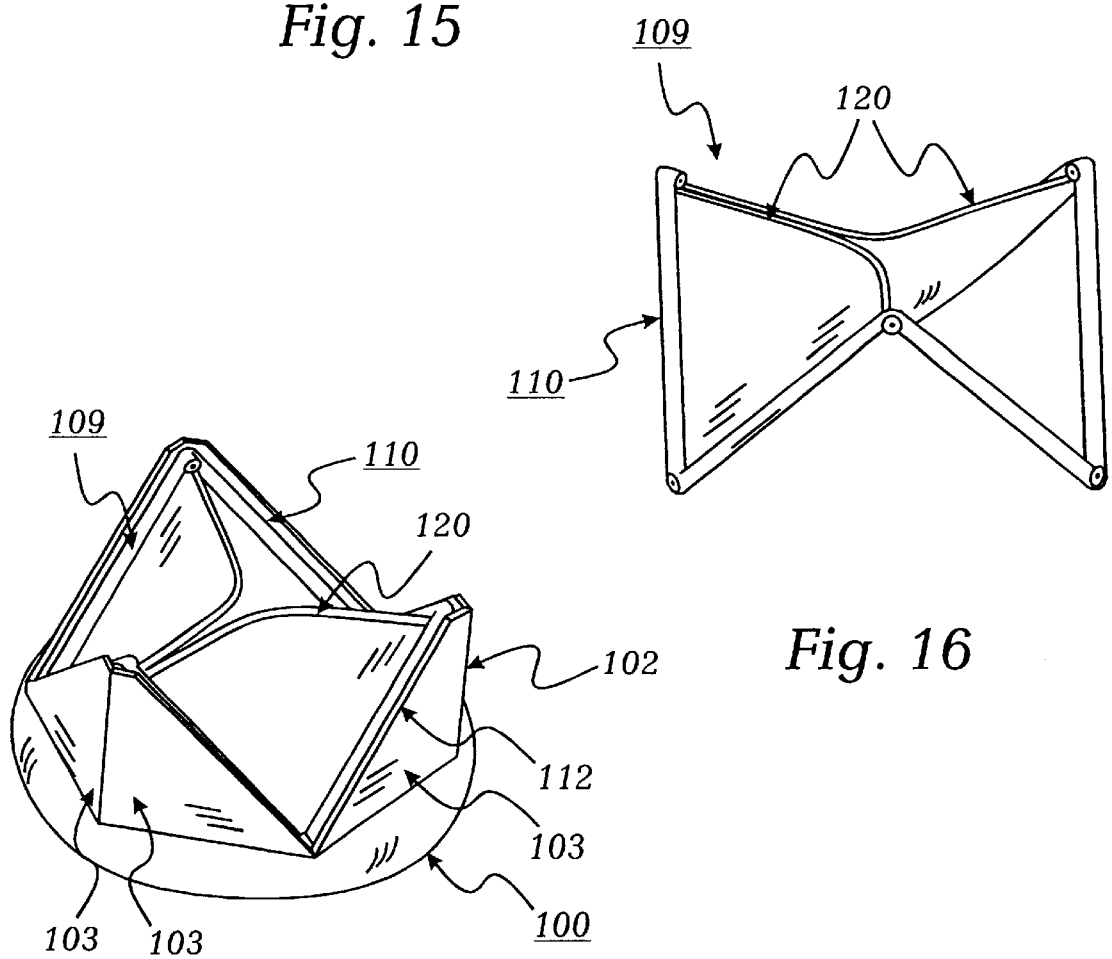
Fig. 16
Fig. 17

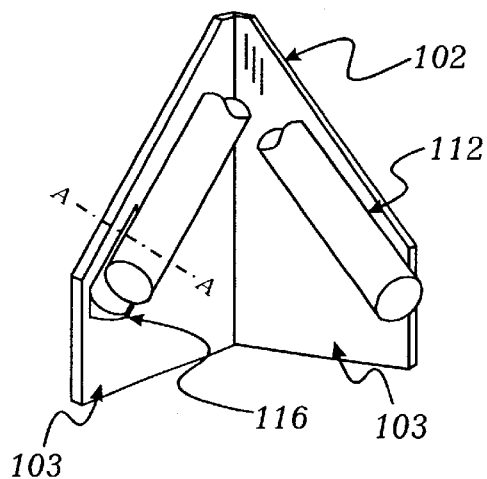
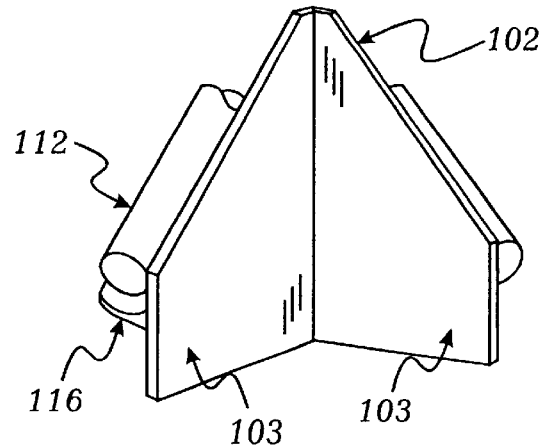
Fig. 19A    Fig. 19B
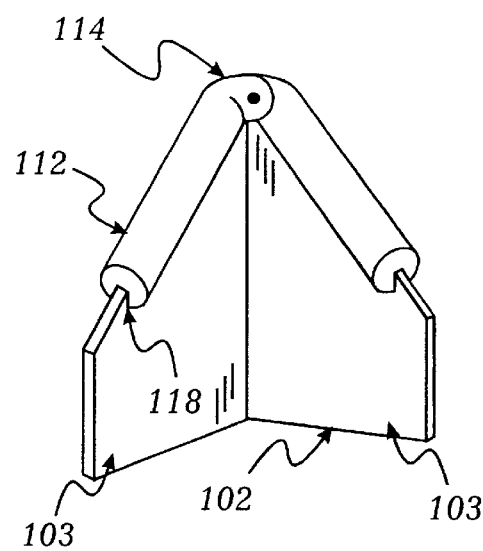
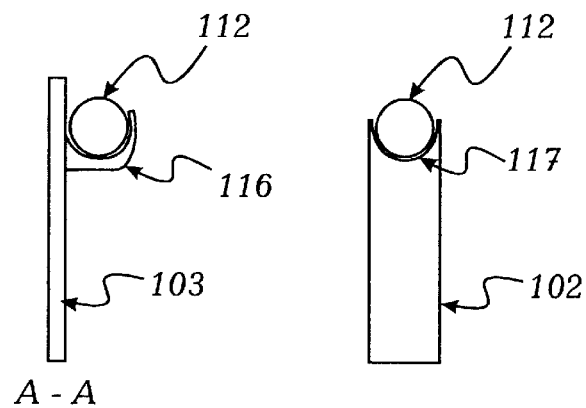
Fig. 19C    Fig. 20A    Fig. 20B

BIOPROSTHETIC CARDIOVASCULAR VALVE SYSTEM

RELATED APPLICATION

This is a continuation-in-part of U.S. application Ser. No. 09/597,918, filed Jun 19, 2000 which is a continuation International Application PCT/US98/27481, with an international filing date of Dec. 23, 1998, which claims the benefit of U.S. Provisional Application No. 60/068,711 filed Dec. 29, 1997.

BACKGROUND OF THE INVENTION

The current practice of inserting artificial heart valves involves cutting the chest open, placing the patient on cardiopulmonary bypass, and surgically inserting the valve into an aorta. This process can take several hours and subjects the patient to significant operative mortality. While the mortality during first valve replacement surgery can be very low (less than 5%), the second surgery carries much greater operative mortality, and the third is even more risky (>15%). Consequently, first and second re-operations to replace a worn out bioprosthetic heart valve are avoided. Since a typical bioprosthesis, or tissue valve, can wear out in 10 years, these valves are typically implanted into patients 60 years old, or older. Younger patients are often recommended a mechanical valve that does not wear out, and typically does not need replacement.

Tissue valves, however, are often preferred over mechanical valves because of their better biocompatibility. Mechanical valves cause blood to clot on their components, and the patient must therefore be chronically treated with anticoagulants to eliminate the risk of major blood clots. Anticoagulant themselves, however, carry a measurable risk of bleeding and thromboembolism and are not an ideal solution. Because tissue valves do not need to be anticoagulated, they are potentially the ideal valve prosthesis, if only their durability were to be improved.

Accordingly, the goal of most tissue valve research and development, has been the improvement in valve durability so that these tissue valves can be put into patients younger than 60 or 65. Because of the operative mortality and morbidity, the objectives of all valve research and development, has been to increase the functional life span of the bioprosthesis so that it can be put into patients only once, and will last the life of the patient. This has thus far been an extremely difficult goal to reach.

There may be another option, however, for the use of tissue heart valves in the younger population. Rather than building valves that last longer, it may be more appropriate to build valves that can be routinely replaced in a way that induces negligible patient morbidity. The objectives would therefore be not to have extremely durable valves, but rather valves that can be easily removed when they begin to fail and new ones inserted. The technologies that make this possible already exist with the advances made in the field of catheter-based endovascular procedures, and the more broad field of Minimally Invasive Surgery (MIS).

The field of MIS is growing at an accelerating pace. The approach involves the use of small surgical probes, cannulas, video cameras and remote staplers and suture drivers that enable surgery to be done without requiring large incisions. Most MIS is done with several small incisions, simply to allow the passage of these instruments into the patients body. The principal advantages of MIS is that the patient is subjected to less surgical trauma and has a dramatically reduced hospital stay, which in turn significantly reduces the operating costs of the clinical center. Current generation minimally invasive procedures are being carried out using endoscopes and long-reaching surgical tools. Typically, the patient's abdomen is inflated with carbon dioxide and the instruments are inserted through small incisions. The surgeons then perform the procedures using endoscopic visualization. For cardiothoracic surgery, similar small incisions are created between the ribs and the heart is placed on bypass using multiple cannulas with balloons that can selectively shut off blood flow through the heart, and direct it through oxygenators.

Other technologies are being developed to do surgery on beating hearts, as to completely avoid placing the heart on bypass. Many of these procedures involve the use of specialized catheters that deploy devices or tools that perform a wide range of procedures on the beating heart. Typical beating heart procedures are endovascular balloon dilatation of arteries and stent placement. Deployment of stents and other permanent devices has become commonplace, but to date, no successful, catheter deployable valve has been developed.

While U.S. Pat. No. 5,545,214 discloses a balloon-deployable tissue valve, the technology is similar to that of stents, and is not ideal for tissue heart valves. The material that anchors the valve in the patient's aortic root is permanently deformed through the bending of metal components, and is not intended to be re-collapsed into its original configuration. Practically the same approach is disclosed in U.S. Pat. No. 5,411,552. U.S. Pat. No. 5,554,185 discloses a means of deploying the valve by inflating of a hollow valve frame with a liquid that hardens. U.S. Pat. No. 5,545,209 describes the use of balloon technology to permanently distend and deploy an endoprosthesis, typically a vascular segment for treating abdominal aneurysm. This patent makes reference to "a tubular prosthesis disposed on said catheter over at least a portion of said balloon." U.S. Pat. No. 5,855,601 describes a prosthetic valve affixed to a wire form that is self expanding, and has a plurality of barbs to anchor the stent in the aorta. The stent itself is of a continuous wire with a zigzag configuration, similar to the endoprostheses described above.

The major concepts disclosed by the above-mentioned patents are similar: the permanent deployment of a bioprosthetic heart valve. A permanently deployed tissue heart valve, whether it is done using MIS technology or not, is subject to the same requirements as conventional tissue valves: it must be very durable. Good durability, however, is not easily attained. The manufacturing process of tissue heart valves is very mature and complex from the quality control point of view, and only minimal improvements in valve durability have been achieved in recent years. Major improvements in valve durability are therefore not expected in the near future.

The present invention addresses the drawbacks discussed above, as well as other problems encountered with the prior art, to provide a bioprosthetic cardiovascular valve system, wherein a valve can be inserted, removed, and re-inserted using minimally invasive surgical techniques.

SUMMARY OF THE INVENTION

According to one aspect of the present invention there is provided a system for minimally invasive removal and re-insertion of a bioprosthetic cardiovascular valve. Preferably, the valve is sufficiently collapsible so as to be able to pass through the lumen of a catheter inserted into the femoral artery, or other large vessel. The collapsed valve is re-expanded when in place in order to fit into a permanent housing or base unit in the patients heart and assumes a fully functioning state. Integral to this system of removal and replacement of a prosthetic valve is an expandable "operative platform" that is deployed near the site of the valve so that it stabilizes the catheters and other instruments during the valve removal and reinsertion process.

In accordance with another aspect of the present invention, there is provided a cardiovascular valve system comprised of a permanent housing or base unit which remains in the patient, and a collapsible valve that engages with the permanent housing, and which is replaceable.

In accordance with a further aspect of the present invention, there is provided a permanent housing or base unit taking the form of a non-collapsible permanent frame which acts as a receptacle for the collapsible valve. The permanent frame includes an integrated sewing ring which is affixed to the patient's aorta or other tissue by means of sutures or staples.

In accordance with another aspect of the present invention, there is provided a collapsible cardiovascular valve including a collapsible frame onto which several leaflets or flexible occluders are affixed, comprised of several articulating or hinged components which have a substantially smaller perimeter when fully collapsed, than when fully expanded.

In accordance with still another aspect of the present invention, there is provided an inflatable or distensible "surgical platform" which can be delivered to a site near the heart in a collapsed state and distended at that site such that it anchors the numerous catheters and devices in space thereby ensuring proper controlled manipulation of their distal ends, when acted upon by controls at their proximal ends.

In accordance with still another aspect of the present invention, there is provided an integrated check valve within the surgical platform that enables controlled ejection of blood from the ventricle during the process of collapsible valve removal and replacement.

In accordance with still another aspect of the present invention, there is provided an integrated filter within the surgical platform that enables the capture of any particulates that may be released during the process of collapsible valve removal and replacement.

In accordance with yet another aspect of the present invention, there is provided a split wall or "monorail" catheter system which can guide larger instruments and devices between the outside of the patient and the surgical platform during the course of a valve replacement procedure.

In accordance with yet another aspect of the present invention, there is provided a tracking and visualization system that can generate accurate images or graphical representation of the catheters and other components on a computer screen so as to accurately represent the position of the real components inside the body of the patient.

Although the bioprosthetic collapsible valve of the present invention may incorporate various number of leaflets, a preferred embodiment of the valve incorporates three (3) valve leaflets.

Although the collapsible valve of the present invention may incorporate a wide range of leaflet materials, such as synthetic leaflets or those constructed from animal tissues, a preferred embodiment of the valve incorporates three (3) valve leaflets constructed from sheets of chemically preserved bovine pericardium.

Although the non-collapsible permanent frame may be constructed from a wide range of materials including metals and plastics, a preferred embodiment of the permanent frame is constructed from a generally stiff, rigid material such as stainless steel, or a polymer.

Although the collapsing mechanism of the collapsible frame may incorporate various means of remaining expanded within the permanent frame of the housing or base unit, one preferred embodiment of maintaining the collapsible frame of the collapsible valve in its expanded state is by means of "snapping" the collapsible frame into slots or clips and/or around protrusions during the expansion process. The collapsible frame is therefore held in an expanded position by means of an interference fit between components.

Although the collapsible valve of the present invention may be expanded by various means, a preferred embodiment of the valve expanding means incorporates an articulating expanding means that does not require the use of balloon technology to expand the collapsible frame.

Although the collapsible frame of the present invention may be collapsed by various means, one embodiment of the valve collapsing means involves expansion beyond its resting configuration, thus unsnapping it from the permanent frame, using a catheter-based manipulation means or handheld tools.

Although the present invention may make use of numerous means of stabilizing the proximal ends of the catheters, a preferred embodiment of the procedure is the use of a stabilizing surgical platform that can be anchored distal to the aortic valve. The surgical platform incorporates slots and fixtures for attaching and holding catheters in slots that stabilize the movement and position of the distal ends of the catheters so that deflection and manipulation of the catheter ends is done in a controlled way.

Although the present invention may make use of numerous means of temporarily augmenting the action of the contracting heart by means of valves, a preferred embodiment of the procedure is the incorporation of an integrated check valve within the surgical platform that becomes functional once the platform is expanded in place. The integrated check valve can be fabricated out of polymer and have one or more occluding leaflets. The leaflets are soft and pliable and enable the passage of catheters and other devices past and through the leaflets. The surgical platform itself can be partially deflated during the valve replacement procedure in order to allow catheters to slide past it to remove or deliver a collapsed valve. The surgical platform may also incorporate an integral sieve or screen to capture and hold any particulates that may be liberated during a valve replacement procedure. The surgical platform may also incorporate an optical, ultrasound, radiographic, magnetic imaging head, or the like, so that close-up detailed images may be obtained during the valve replacement procedure.

Although the present invention may make use of numerous catheters to deliver the components of the collapsible valve system into the desired site, one embodiment of the procedure is the use of multiple catheters and sheaths small enough to be inserted into the femoral artery without exposing the femoral artery to perform a "cut-down".

Although the present invention may make use of numerous imaging or localization techniques, one preferred embodiment of the procedure is the use of a ultrasonic or electromagnetic sensors affixed to the catheters and components such that their position can be detected and tracked in 3-D space, in sufficient spatial and temporal resolution and precision, so as to make the procedure easy and accurate.

Another visualization technique is bi-plane radiography or intra-cardiac echocardiography.

As can be seen by those skilled in the art, an advantage of the present invention is the provision of a valve system that allows for safe and convenient removal and replacement of a collapsible valve when it begins to fail.

Another advantage of the present invention is the provision of an expandable, re-collapsible tissue-based cardiovascular valve.

Another advantage of the present invention is the provision of an expandable, re-collapsible valve that is small enough to be delivered by catheters by way of a percutaneous puncture.

Another advantage of the present invention is the replacement of a recollapsible valve by way of conventional or minimally invasive cardiac surgery.

Still another advantage of the present invention is the provision of a catheter-based valve delivery system.

Still another advantage of the present invention is the provision of a valve delivery system consisting of surgical tools that can remove and deliver a re-collapsible valve by way of small incisions in the blood vessels that emerge from the heart, or in the wall of the heart itself.

Still another advantage of the present invention is the provision of a stable surgical platform within which catheter-based manipulators can be securely anchored so that intracardiac procedures can be properly executed.

Yet another advantage of the present invention is the provision of a synthetic valve integrated with the surgical platform to act as a temporary check valve while the expandable, re-collapsible tissue-based cardiovascular valve is being replaced.

Yet another advantage of the present invention is the provision of a mesh integrated with the surgical platform to act as a sieve that captures any particulates that may be liberated during the valve replacement procedure.

Yet another advantage of the present invention is the provision of a slotted catheter sheath that can act as a "monorail" guide to shuttle components along the outside of the sheath between the exit/entry port of the patient and the surgical platform within the heart.

Yet another advantage of the present invention is the provision of a ultrasound or electromagnetic catheter guidance system that can track the position and motion of the catheters and devices during the procedure and display images of the system components on a video display monitor, so as to make the procedure easy and accurate.

Still other advantages of the invention will become apparent to those skilled in the art upon a reading and understanding of the following detailed description, and accompanying drawings.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein:

FIG. 7A shows an exploded view of a catheter-based valve delivery system, including a surgical platform and numerous accessory devices and catheters, according to one preferred embodiment of the present invention;

FIG. 7B shows an enlarged partial sectional view of a slotted catheter sheath, according to a preferred embodiment of the present invention;

FIG. 7C shows an enlarged partial sectional view of an inner catheter, according to a preferred embodiment of the present invention;

FIG. 7D is a schematic representation illustrating the operation of gripping means, in accordance with a preferred embodiment of the present invention;

FIG. 9A illustrates a front view of the cardiac anatomic site;

FIG. 9B illustrates a top view of the cardiac anatomic site shown in FIG. 9A;

FIG. 9C is a simplified enlarged front view of the cardiac anatomic site shown in FIG. 9A.

FIG. 15 shows a perspective view of the collapsible frame of FIGS. 12–14, in an expanded configuration, as an engaged with the permanent base unit shown in FIGS. 10 and 11.

FIG. 16 shows a perspective view of the collapsible cardiovascular valve in its expanded position (including the collapsible frame of FIGS. 12–14 and two valve leaflets, wherein the third valve leaflet is omitted for clarity).

FIG. 17 shows a perspective view of the cardiovascular valve system according to an alternative embodiment of the present invention, wherein the collapsible valve (including the collapsible frame of FIGS. 12–14 and two valve leaflets, wherein the third valve leaflet is omitted for clarity) is shown in an expanded position, as engaged with the permanent base unit shown in FIGS. 10 and 11.

FIG. 19A shows a partial perspective view illustrating a method by which a collapsible frame of the collapsible valve is engaged with a permanent frame of the permanent base unit.

FIG. 19B shows a partial perspective view illustrating another method by which a collapsible frame of the collapsible valve is engaged with a permanent frame of the permanent base unit.

FIG. 19C shows a partial perspective view illustrating still another method by which a collapsible frame of a collapsible valve is engaged with a permanent frame of the permanent base unit.

FIG. 20A shows a cross-sectional view taken along line A—A of FIG. 19A.

FIG. 20B illustrates yet another alternative method by which a collapsible frame of a collapsible valve is engaged with a permanent frame of the permanent base unit.

FIG. 24 illustrates the cardiovascular valve system according to the alternative embodiment of FIG. 22, showing the collapsible valve fitted over a catheter body and snares positioned over retaining clips.

DETAILED DESCRIPTION OF THE PREFERRED EMBODIMENT

The detailed description set forth below in connection with the appended drawings is intended merely as a description of the presently preferred embodiments of the invention, and is not intended to represent or limit the form in which the present invention can be constructed or used. The description sets forth the function and sequence of steps for construction and implementation of the invention. It is to be understood that the same or equivalent functions and sequences may be accomplished by different embodiments that are also intended to be encompassed within the spirit and scope of the invention. For example, a similar valve system can be used to insert a similar collapsible valve (e.g., a prosthetic valve or endoprosthesis) into the mitral position, the pulmonary and tricuspid positions of the heart or an other expandable prosthetic device into any other location within the vasculature or an organ of any patient. Moreover, while a preferred embodiment of the present invention is illustrated herein as a cardiovascular valve system for use in connection with the heart, the present invention is contemplated for use as a valve system with other parts of the cardiovascular system.

In accordance with a preferred embodiment of the present invention, a system for inserting a valve into the aortic position using a catheter-based, endovascular, minimally invasive techniques is generally comprised of the following:

(1) A valve that can be collapsed for insertion, expanded when in place so as it fits securely within a permanent housing that remains in the patient, and collapsed again for removal once the tissue component of the collapsible valve wears out.

(2) A multi-component, catheter-based system for the percutaneous, removal and delivery of a collapsible valve.

(3) A set of surgical tools that have fixtures similar to those at the ends of the catheters, for the surgical removal and delivery of a collapsible valve.

(4) A device tracking, visualization system to enable this procedure to be done with high precision and minimal chance of complications.

I. Construction of the Collapsible Cardiac Valve and Frame

Figure 1:
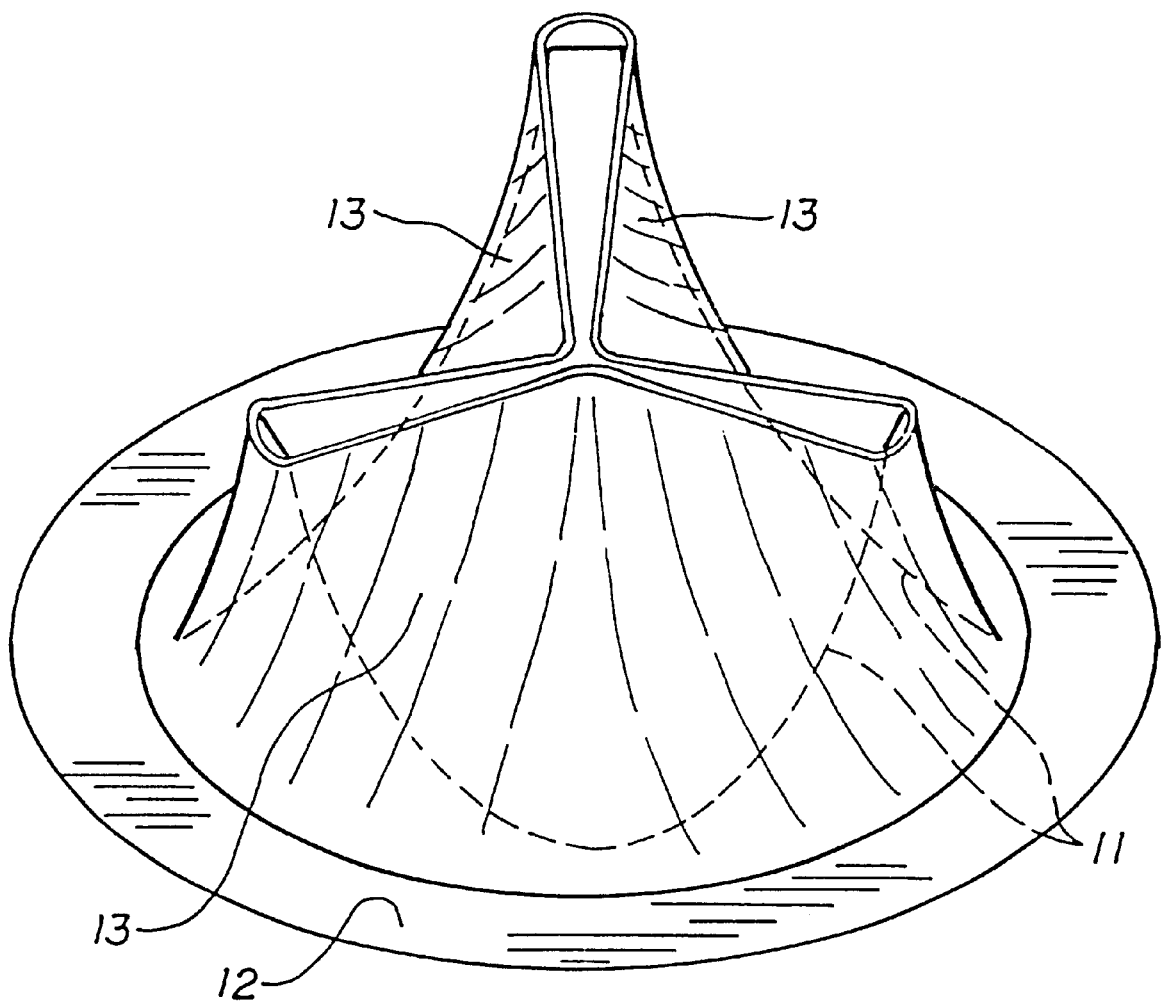
FIG. 1 shows images of typical prior art bioprosthetic valve having leaflets made of bovine pericardium mounted on a supporting stent.

One aspect of the present invention is directed to an expandable, recollapsible tissue-based valve system. With reference to FIG. 1 a typical prior art tissuebased prosthetic valve includes three (3) leaflets 13 sewn to and supported on a metal or polymer frame or stent 11. One aspect of the present invention is directed to a collapsible valve system generally comprised of two components: (i) a permanent outer frame that is affixed to the patient using conventional sutures or staples (FIG. 2), and (ii) an inner collapsible valve (FIGS. 3A–3C and 4A–4B) that mates with the outer frame and includes valve leaflets. The inner collapsible valve is normally collapsed, is delivered against the previously inserted outer frame, expanded, and locked in place. Importantly, the inner collapsible valve may be collapsed again and removed. A new inner collapsible valve is then inserted into the original outer frame, to resume the function of the prosthesis.

Figure 2:
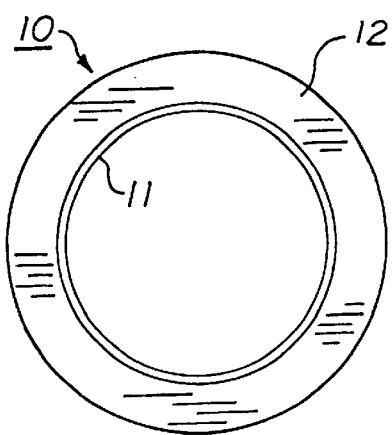
FIG. 2 shows a top plan view of the permanent frame, according to a preferred embodiment of the present invention.

With reference to FIG. 2, there is shown a preferred embodiment of a permanent base unit taking the form of an outer frame 10. Outer frame 10 is generally comprised of a rigid ring 11, and a soft sewing ring 12 for attachment of the outer frame 10 the wall of the aorta or other structure within the heart.

Referring now to FIGS. 3A–3B and 4A–4B, there is shown a preferred embodiment of the collapsible valve 20. Collapsible valve 20 is generally comprised of an articulating inner frame 21 having a plurality of projections or stent posts 22, and a plurality of leaflets (not shown). It should be understood that the leaflets are mounted to the stent posts 22 in a manner similar to that shown in FIG. 1, and movable between an occluded position and an open position. The inner frame 21 that supports the plurality of leaflets is formed of a plurality of articulated segments 24 (typically 6 or more segments), that fold together in a way so that the total outer diameter of the inner frame is reduced for insertion, as best seen in FIG. 3C. The articulated segments 24 are typically rigid structures that snap into a locked position as they are completely unfolded during deployment. Articulated segments 24 articulate around pin hinges 25 (FIGS. 3B–3C) or other flexible strips 28 (FIGS. 4A–4B), means that can assure a flexible attachment between any adjacent segments. It will be appreciated that other means for articulating are also suitable, including ball and socket joints.

The process of collapse and expansion involves a "snapping" action that produces some elastic material deformation of the segments 24 and/or the hinges 25 and/or the strips 28, as the segments articulate between their fully expanded configuration and their partially collapsed configuration. This is achieved by means of an interference fit between opposing segments that articulate near each other. The provision for the snapping process is so that once expanded, the inner frame remains expanded under its own internal tension, and does not collapse due to undue internal or external force applied to it during normal activity.

Figure 5:
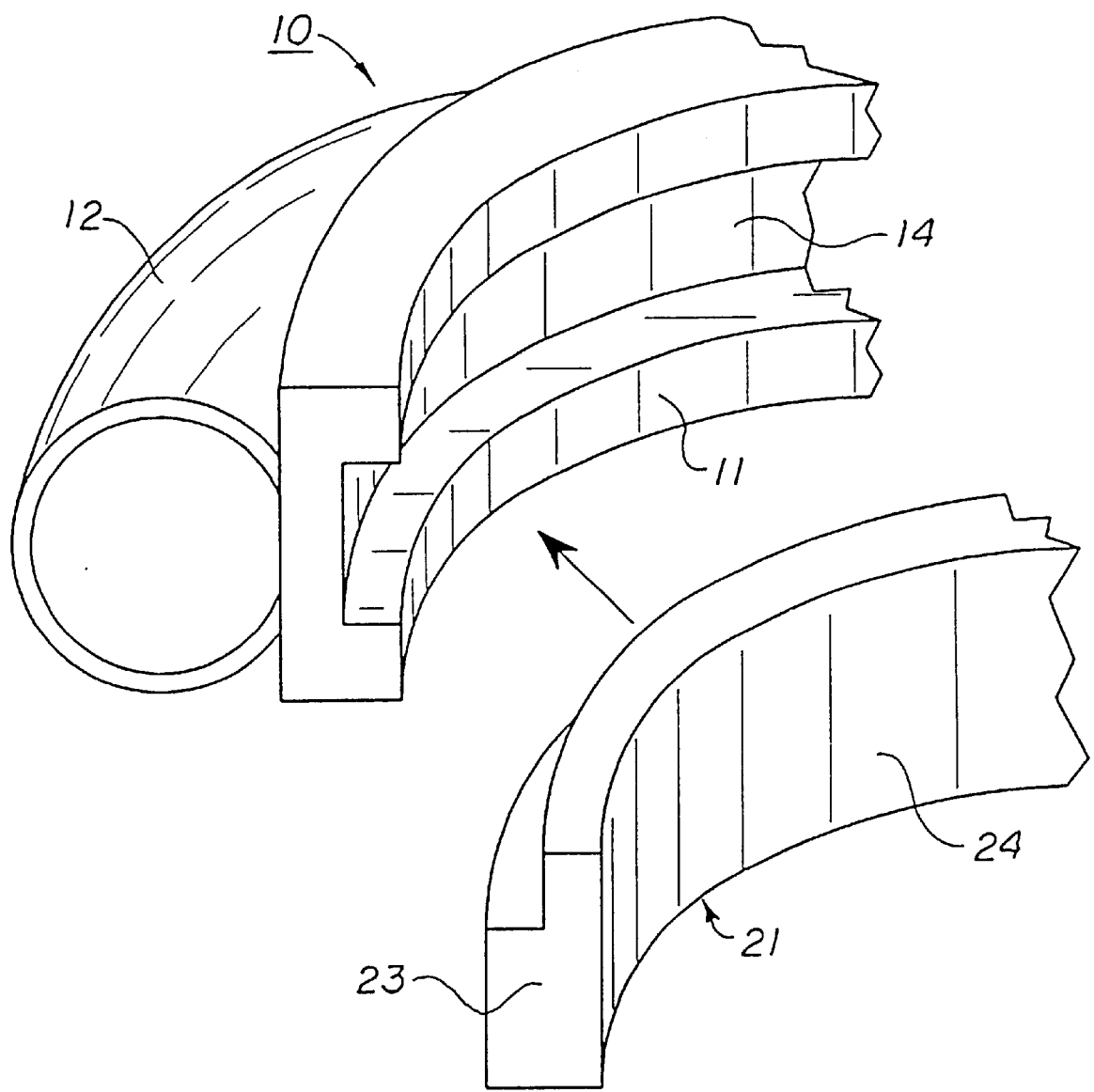
FIG. 5 shows an enlarged partial sectional view of the collapsible and noncollapsible permanent frames, to illustrate the mating surfaces thereof.

Referring now to FIG. 5, the inner frame 21 is held in tight opposition against the rigid ring 11 of the outer frame 10 by means of a generally annular groove 14 on the inner surface of the rigid ring 11, into which each of the articulating segments 24 fit when the inner frame 21 is expanded. Accordingly, annular groove 14 provides a means for interfacing and attaching outer frame 10 with inner frame 11. It will be appreciated that articulated segments 24 include a flange portion 23, which is dimensioned to be received into groove 14. The fit between flange portion 23 of inner frame 21 and groove 14 of rigid ring 11 is such that the collapsible valve 20 cannot be withdrawn from the outer frame 10 when the inner frame 21 is expanded, and can only be withdrawn when the inner frame 21 is collapsed. It should be appreciated that other means for interfacing inner frame 21 with outer frame 10 are also suitable.

Figure 10:
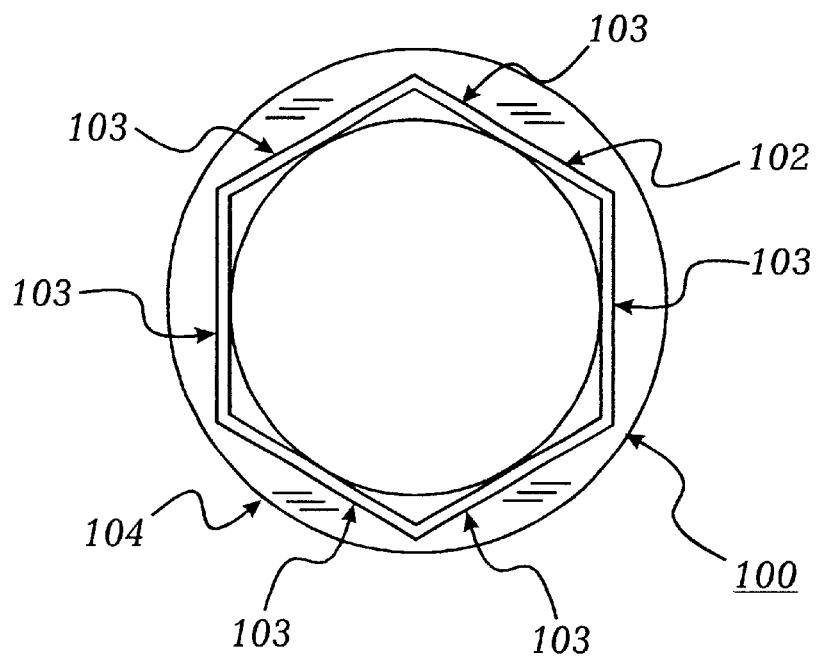
FIG. 10 shows a top plan view of a permanent base unit, according to an alternative embodiment of the present invention.
Figure 11:
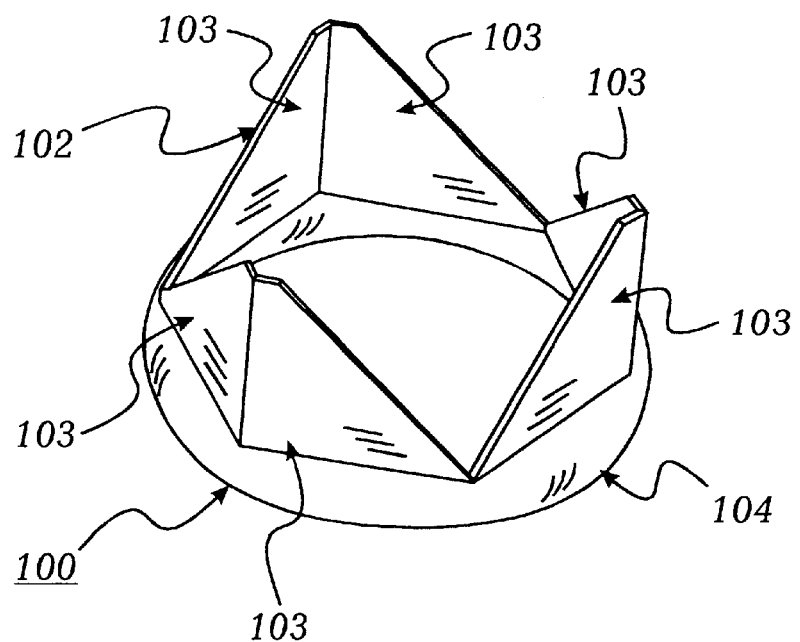
FIG. 11 shows a perspective view of the permanent base unit, as shown in FIG. 10.

A collapsible cardiovascular valve system according to an alternative embodiment of the present invention will now be described with reference to FIGS. 10–20. Referring to FIGS. 10 and 11, there is shown a permanent base unit 100 according to an alternative embodiment of the present invention. Permanent base unit 100 is generally comprised of a permanent frame 102 and a generally annular soft sewing ring 104. Sewing ring 104 is used to attach permanent base unit 100 with the wall of the aorta or other structure within the heart, as well known to those skilled in the art. Permanent frame 102 includes a generally circular arrangement of outward extending generally triangular flat rigid plates 103, which when arranged circumferentially, define a valve orifice. A generally v-shaped opening is defined by adjacent pairs of plates 103. Permanent frame 102 acts as a receptacle for a collapsible valve, described below.

Figure 12:
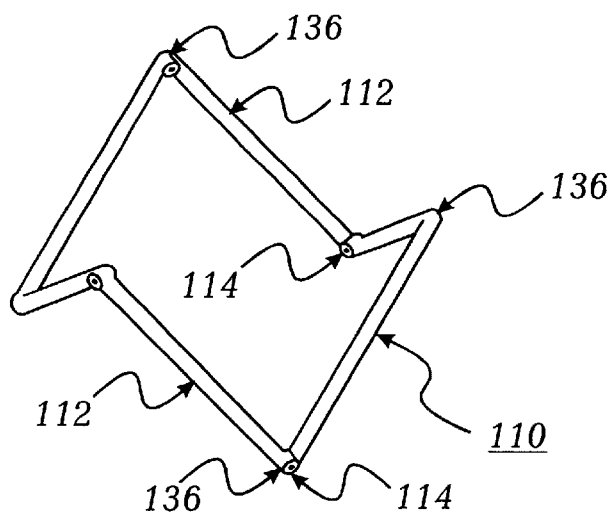
FIG. 12 shows a perspective view of a collapsible frame (in an expanded position) of a collapsible valve, according to an alternative embodiment of the present invention.
Figure 13:
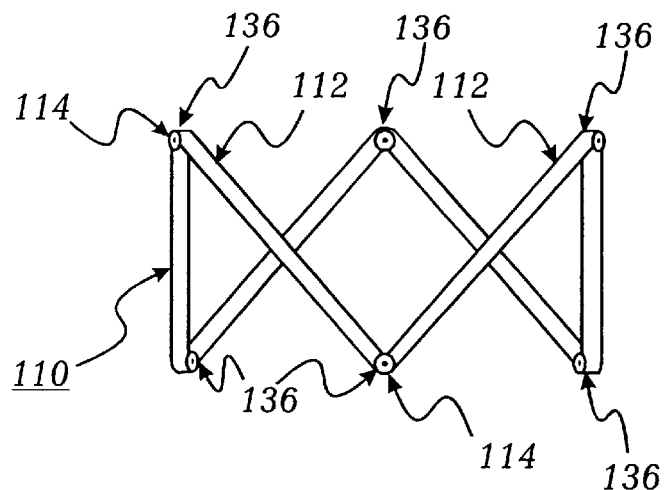
FIG. 13 shows a side view of the collapsible frame, as shown in FIG. 12.
Figure 14:
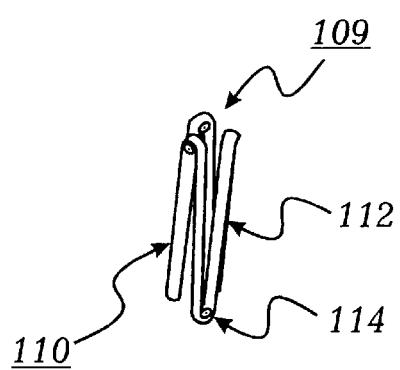
FIG. 14 shows a perspective view of the collapsible frame of FIGS. 13 and 14 (in a collapsed position), according to an alternative embodiment of the present invention.

A collapsible valve 109 according to an alternative embodiment of the present invention will now be described with reference to FIGS. 12–17. Collapsible valve 109 is generally comprised of an collapsible frame 110 and at least one valve leaflet 120. FIGS. 12–15 illustrate collapsible valve 109 without valve leaflets 120, in order to more clearly illustrate collapsible frame 110. Furthermore, FIGS. 12–13 and 15–17 illustrate collapsible valve 109 in an expanded position, while FIG. 14 illustrates collapsible valve 109 in a collapsed position.

Collapsible frame 110 is generally comprised of a plurality of articulating generally linear rigid struts 112 connected together at their distal ends 136 by way of an articulation member 114. Struts 112 fold together in a manner to minimize the total outer diameter of collapsible frame 110 in a collapsed position, to facilitate insertion and removal of valve 109.

Figure 3B:
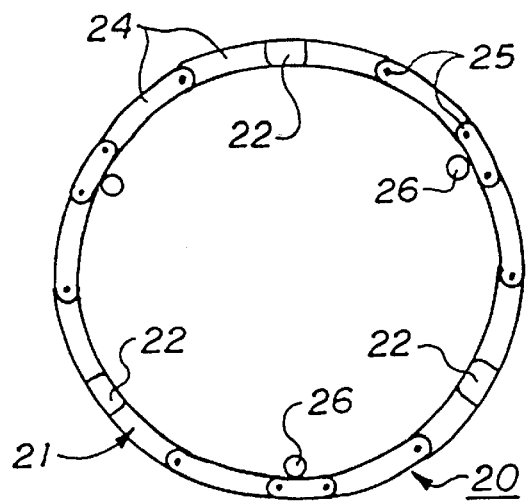
FIG. 3B shows a top plan view of the collapsible frame shown in FIG. 3A.
Figure 4A:
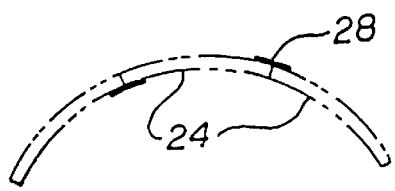
FIG. 4A illustrates a collapsible frame in an expanded position, in accordance with an alternative embodiment.
Figure 3C:
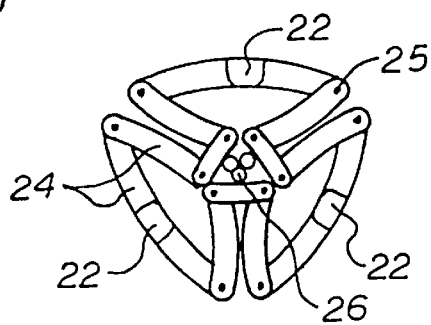
FIG. 3C shows a top plan view of the collapsible frame shown in FIG. 3A, in a collapsed position.
Figure 4B:
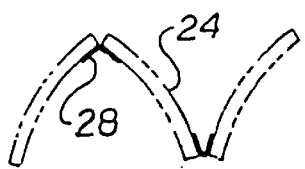
FIG. 4B illustrates the collapsible frame of FIG. 4A, in a collapsed position.

Articulation member 114 preferably includes (but is not limited to) pivot members, pin hinges 25 (such as shown in FIGS. 3B–3C), flexible strips 28 (such as shown in FIGS. 4A–4B), ball and socket joints, or other means that allow for a flexible articulation between adjacent struts 112.

As illustrated in FIGS. 15–17, collapsible frame 110 may be engagingly opposed against the inner surface of rigid plates 103 when it is in an expanded position. In this regard, plates 103 are dimensioned to correspond with the dimensions of collapsible frame 110 in its expanded position. Accordingly, the profile formed by plates 103 is matched to correspond to the profile formed by collapsible frame 110 when collapsible frame 110 is in an expanded position. Thus, struts 112 of collapsible frame 110 abut the inner surface of plates 103 (FIG. 15). If collapsible frame 110 is comprised of six rigid struts 112 (as best shown in FIGS. 12–13), then permanent frame 102 is comprised of six appropriately-sized plates 103. In accordance with a preferred embodiment, three valve leaflets 120 (only two are shown for clarity in FIGS. 16 and 17) are suspended from collapsible frame 110. Thus, when collapsible frame 110 is expanded, a fully functioning valve is formed.

Figure 18A:
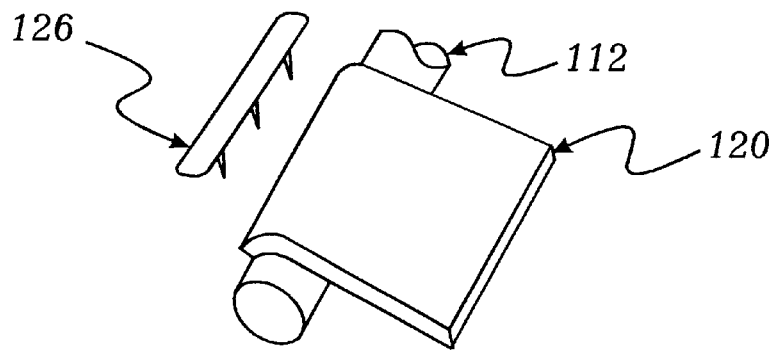
FIG. 18A shows a perspective view illustrating one method by which valve leaflets are connected with a collapsible frame.
Figure 18B:
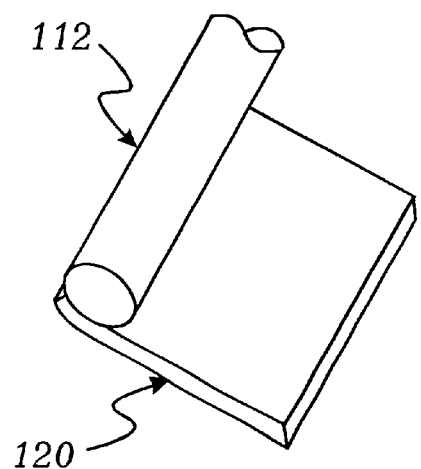
FIG. 18B shows a perspective view illustrating another method by which the valve leaflets are connected with a collapsible frame.
Figure 18C:
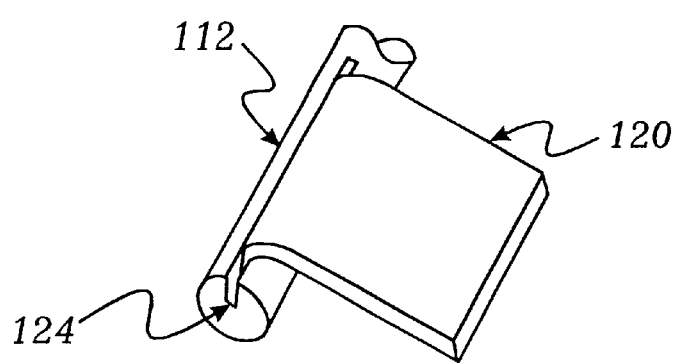
FIG. 18C shows a perspective view illustrating still another method by which valve leaflets are connected with a collapsible frame.

Referring now to FIGS. 18A–18C, there are shown several alternative approaches for attaching valve leaflets 120 to collapsible frame 110. These approaches include valve leaflets 120 affixed to struts 112 by wrapping valve leaflets 120 over the top upper surface of struts 112 (FIG. 18A), under the bottom lower surface of struts 112 (FIG. 18B), or into a slot 124 formed in struts 112 (FIG. 18C). Valve leaflets 120 may be connected to struts 112 by way of sutures passing through holes formed in struts 112, or by way of pins or tacks, either individual or part of a strip of material 126, that pass through leaflet 120, and insert and lock into strut 112 (FIG. 18A). It should be appreciated that struts 112 of collapsible frame 110 mate tightly against plates 103 (FIGS. 15 and 17) in the expanded position, so as to prevent any blood from leaking between struts 112 and plates 103.

As will now be described with reference to FIGS. 19A–19C, there are several alternative methods by which collapsible frame 110 may be retained in tight opposition against plates 103 of permanent frame 102. These approaches include (but are not limited to) a provision for struts 112 to be positioned and attached to: (a) the inner surface of plates 103 (FIG. 19A), (b) the outer surface of plates 103 (FIG. 19B ), or (c) the top edge of plates 103 (FIG. 19C). In each approach, struts 112 are in engaged with plates 103, thus preventing blood from leaking between them.

Struts 112 may be retained by appropriately shaped supports or gussets 116 that project from the surface of plates 103, either along the entire length of contact between strut 112 and plate 103, or only part of the way (FIGS. 19A and 19B). FIG. 20A provides a cross-sectional view of permanent frame 102 taken along line A—A of FIG. 19A. Gusset 116 is shown affixed to the inner surface of plate 103. As can be seen in FIG. 20A, gusset 116 is dimensioned such that it accepts strut 112 by means of a snap fit. A similar gusset 116 is affixed to the outer surface of plate 103 in the embodiment shown in FIG. 19B.

In the embodiment shown in FIG. 19C struts 112 are slotted along their length, so as to fit onto the top edge of plate 103, an appropriately sized slot 118 is formed in struts 112. In this regard, slots 118 act to retain collapsible valve 109 in engagement with permanent frame 102. It should also be appreciated that plates 103 are appropriately dimensioned at their top edge to provide the necessary clearance, so as not to cause interfere with articulation member 114.

FIG. 20B illustrates yet another alternative means for engaging struts 112 with permanent frame 102. In this regard, plates 103 are dimensioned to be sufficiently thick such that a channel 117 can be formed in the top edge thereof. Channel 117 is dimensioned to receive strut 112 by means of a snap fit, thus retaining collapsible valve 109 in engagement with permanent frame 102. Struts 112 are received into channels 117 formed in the top edge of plates 103, thus securing collapsible frame 110 to the top edge of plates 103 in a manner similar to the embodiment shown in FIG. 19C.

Figure 21:
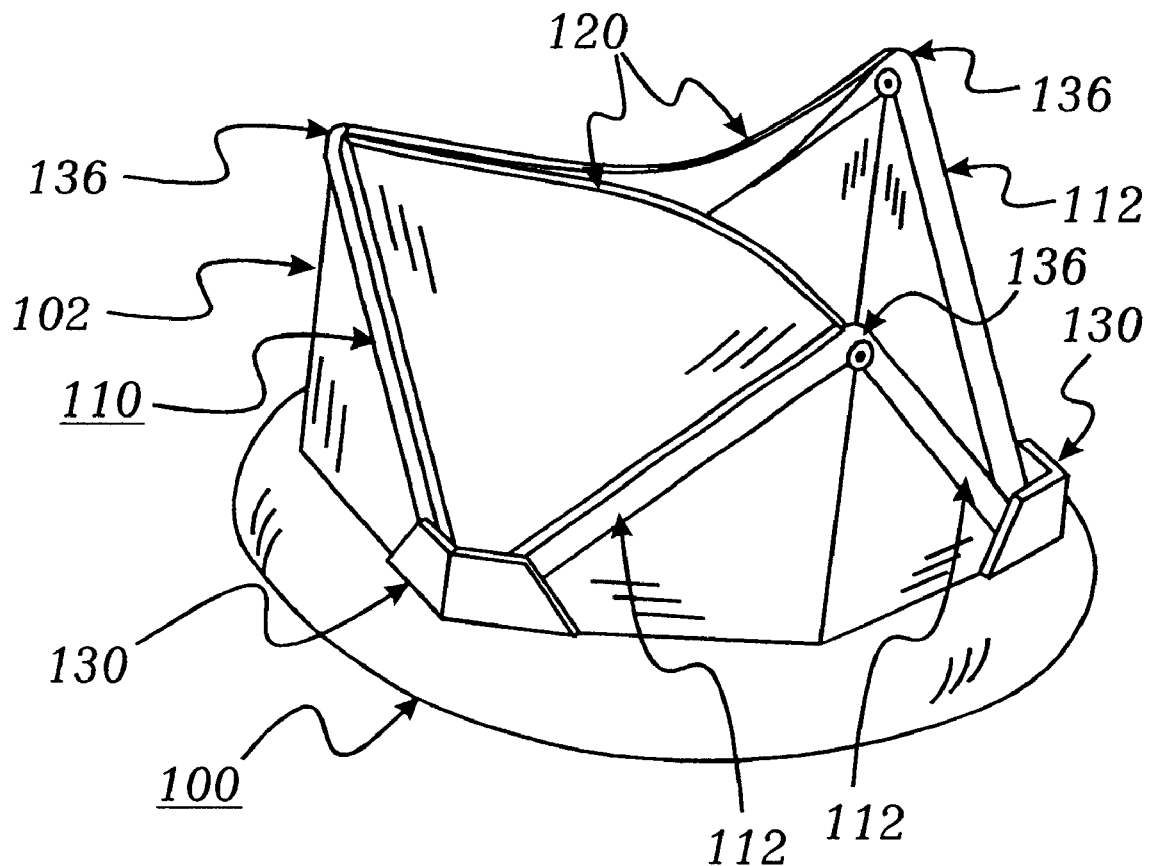
FIG. 21 shows a perspective view of a cardiovascular valve system comprised of a collapsible valve (including the collapsible frame of FIGS. 12–14 and two valve leaflets, wherein the third valve leaflet is omitted for clarity) and a permanent base unit, according to still another alternative embodiment, wherein the collapsible frame is fitted over the permanent frame.

Referring now to FIG. 21, there is shown another embodiment of base unit 100, wherein permanent frame 102 includes holding plates 130 that are positioned adjacent to rigid plates 103, to form a slot or gap for receiving strut 112. Holding plates 130 capture and hold in place the bottom ends of struts 112 of collapsible frame 110, in the embodiment wherein struts 112 of collapsible frame 110 are engaged with the outside of rigid plates 103, such as shown in FIG. 19B. In this regard, hold plates 130 act as additional retainers for retaining collapsible valve 109 in engagement with permanent frame 102.

Figure 22:
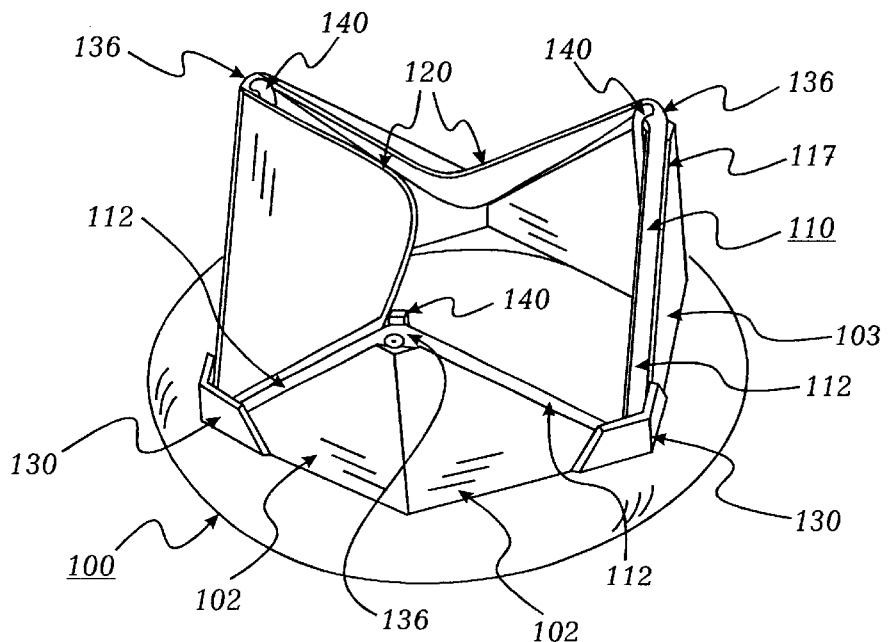
FIG. 22 illustrates a cardiovascular valve system according to another alternative embodiment.
Figures 23A, 23B, 23C:
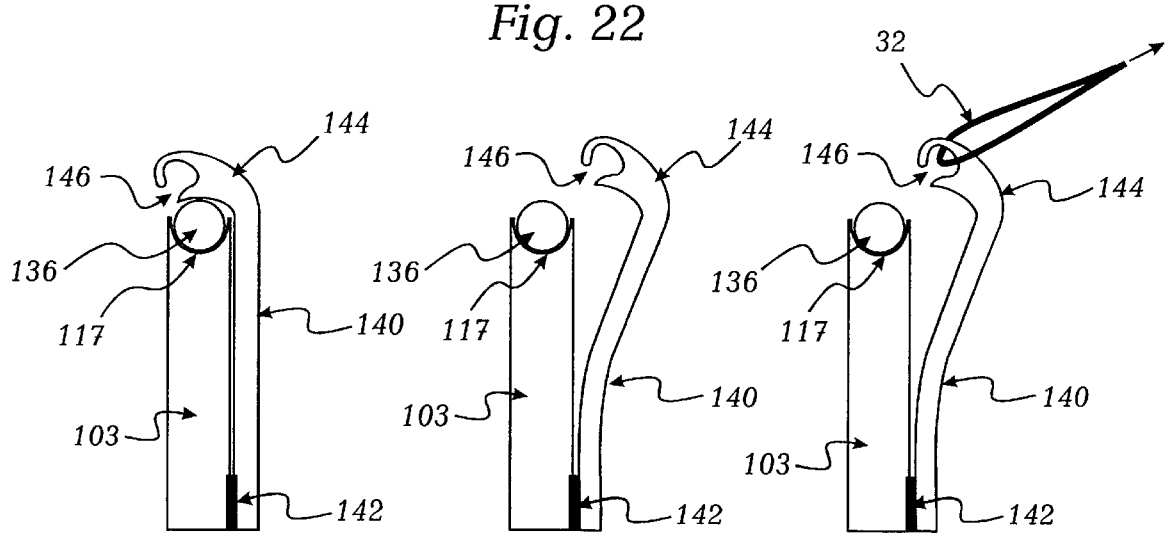
FIGS. 23A–23C and 24 illustrate operation of a retaining clip of the cardiovascular valve system shown in FIG. 22.
Figure 24:
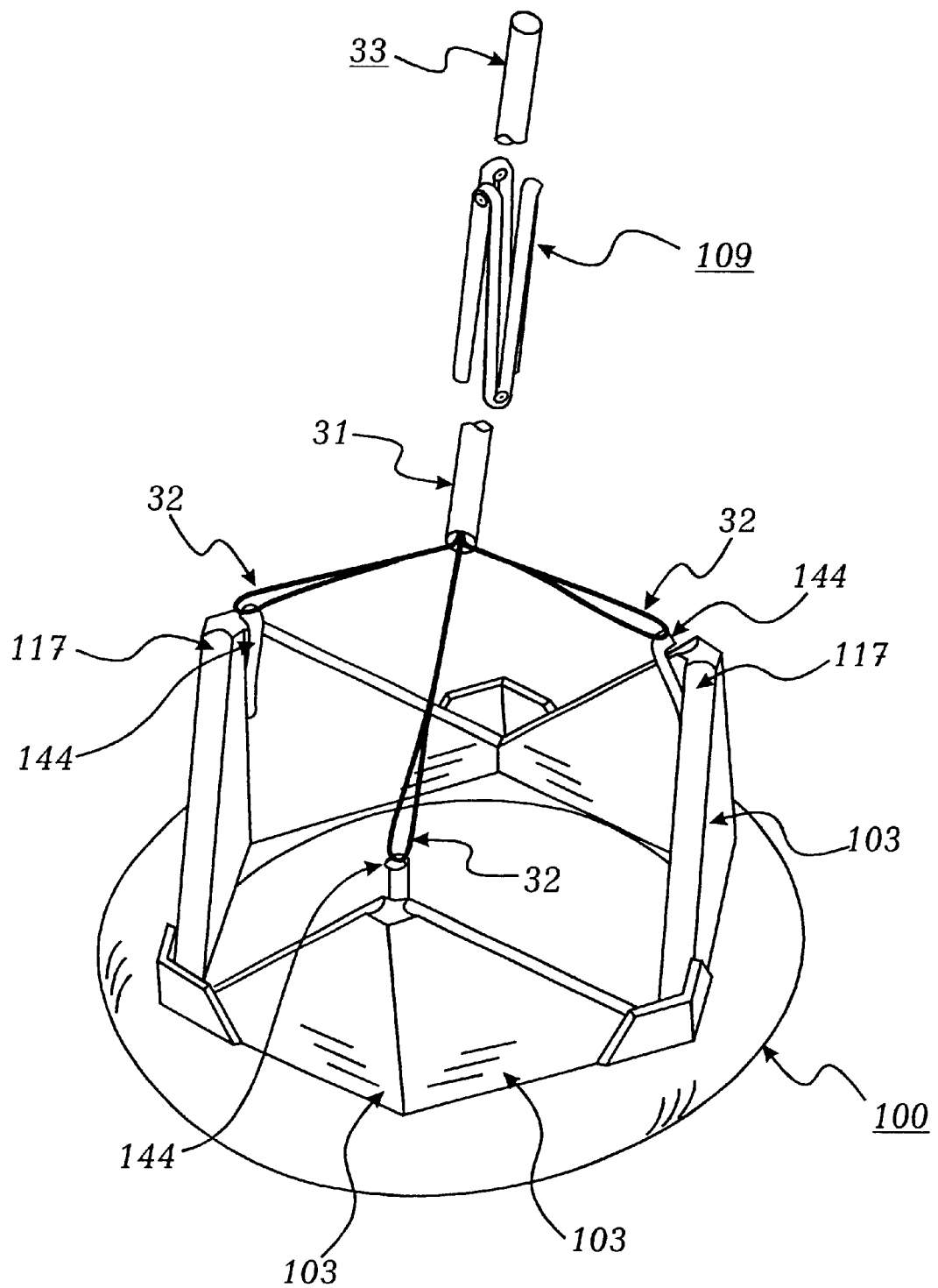

Referring now to FIGS. 22–24, there is shown yet another alternative embodiment of the cardiovascular valve system, wherein yet another means is used for retaining collapsible valve 109 in engagement with permanent frame 102. In addition to using holding plates 130 to capture and hold in place the bottom ends of struts 112 (as in the embodiment shown in FIG. 21), a channel 117 may be formed along some or all the length of the upper surface of plates 103 of permanent frame 102. Channel 117 is dimensioned to receive struts 112 of collapsible frame 110. A plurality of retaining clips 140 are provided to secure struts 112 within channel 117. Retaining clips 140 are movable between a retain position and a release position, and are biased to the retain position. In the retain position, struts 112 are retained within channel 117. In a release position, struts 112 may be removed from channel 117, or inserted into channel 117. Preferably, retaining clips are formed of an elastic material to facilitate movement between the retain and release positions.

With particular reference to FIGS. 23A–23C, it can be seen that retaining clips 140 are located adjacent the inner surface of plates 103 at lower end 142 thereof, and include a projection portion 144 which projects up and over the top surface of struts 112, at ends 136 thereof. Projection portion 144 may have a generally curved shape. Projection portion 144 prevent struts 112 from disengaging from channel 117 by projecting over the top surface of strut 112 at end 136. Consequently, collapsing collapsible frame 110 requires retaining clip 140 to be elastically bent away from the inner surface of plate 103 (i.e., moved to a release position) so as to allow struts 112 to be disengaged from channel 117 (FIG. 23B).

Figure 6A:
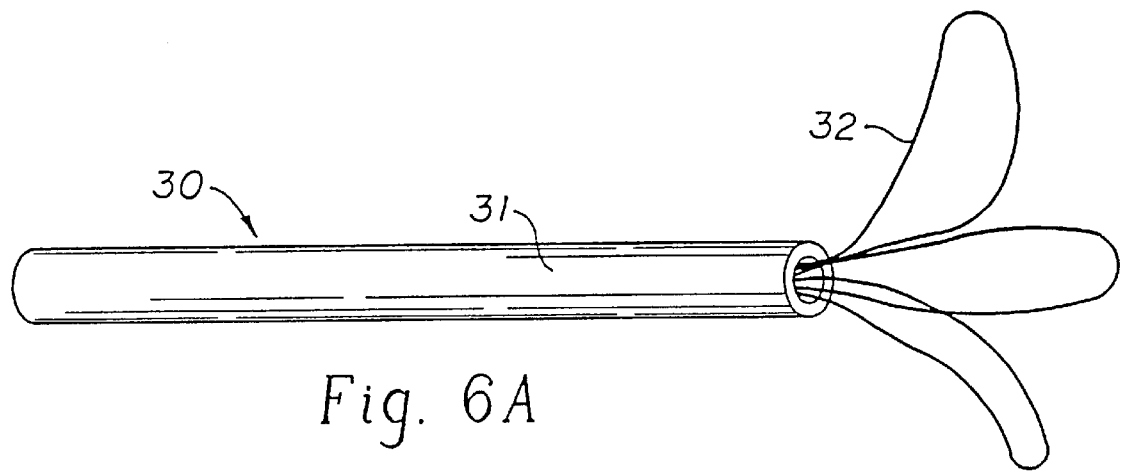
FIG. 6A shows an exemplary embodiment of a valve collapsing catheter.

FIG. 23C illustrates an exemplary method for bending retaining clip 140 away from the inner surface of plate 103. In this regard, a suitable snare 32 is engaged with a recess or notch 146 formed at the distal end of projection portion 144. Snare 32 applies tension to projection portion 144 by being pulled back into a catheter 31 (see FIG. 6A). Notch 146 is dimension so as to prevent snare 32 from slipping out during all possible angles of function.

The process by which retaining clips 140 are captured by snares 32 and pulled to a release position by drawing the snares into a catheter body 31, will now be described with reference to FIG. 24. It should be appreciated that collapsible valve 109 may be fitted over catheter body 31, prior to being expanded and fitted to permanent base unit 100. Collapsible valve 109 may be fitted over catheter body 31 in a very compact, space efficient way.

Figure 27A:
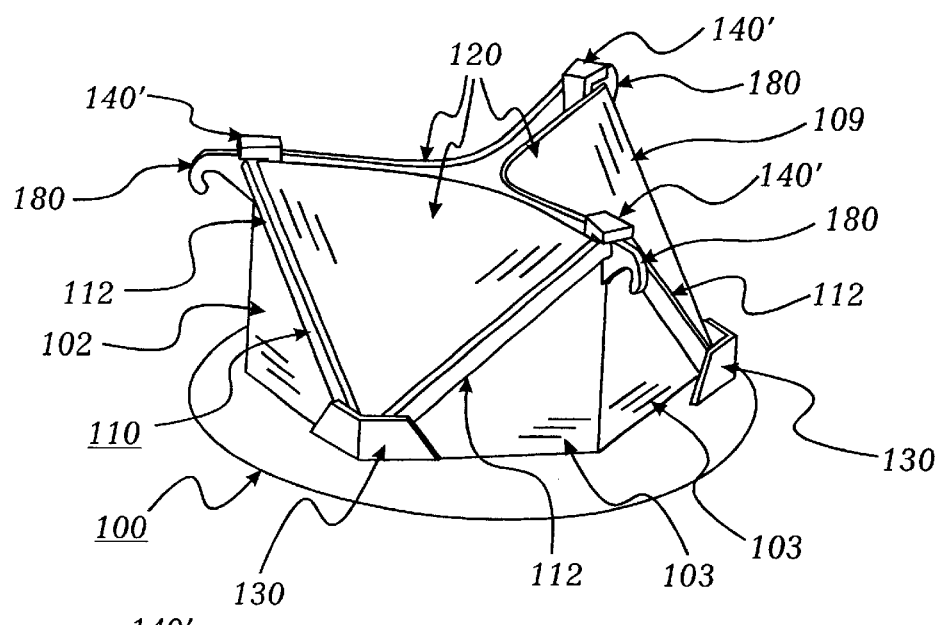
FIGS. 27A–27C illustrate a cardiovascular valve system according to yet another alternative embodiment.
Figure 27B:
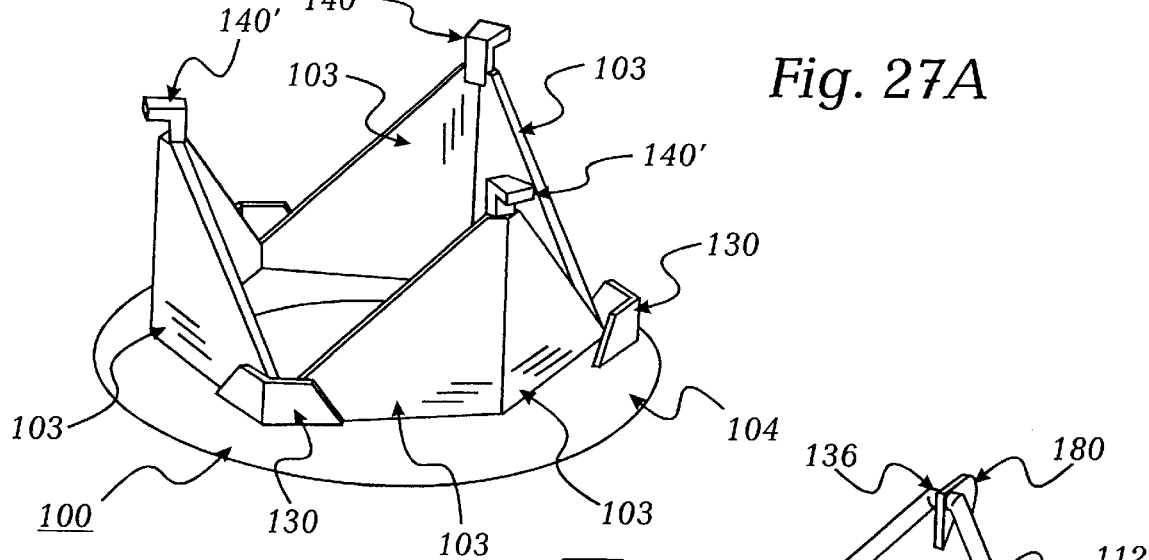
Figure 27C:
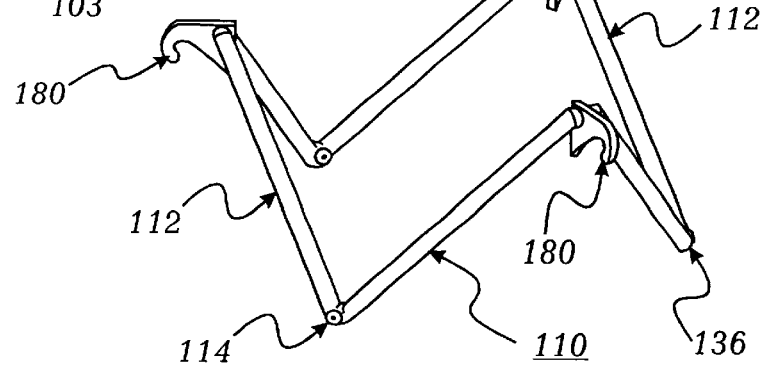
Figure 28:
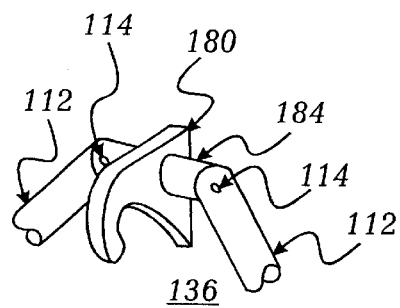
FIGS. 28 and 29A–29C illustrate operation of an expanding lever for disengaging a collapsible valve from a base unit.

Referring now to FIGS. 27–29, there is shown yet another alternative embodiment of the cardiovascular valve system. Yet another means is used to retain the collapsible valve 109 in engagement with permanent frame 102. In accordance with this embodiment of the cardiovascular valve system, struts 112 of collapsible frame 110 are fitted against the outer surface of the plates 103, as in FIG. 19B. In addition to using holding plates 130 to capture and hold in place the bottom ends 136 of struts 112 (as in the embodiment shown in FIG. 21), base unit 100 is fitted with retaining members 140' that protrude over the top ends 136 of struts 112. In accordance with a preferred embodiment, retaining members 140' are comprised of two generally perpendicular portions. Unlike the deflectable retaining clips 140 of FIG. 23, retaining members 140' are generally rigid and affixed to plates 103 of permanent frame 102.

As shown in FIG. 27A, top ends 136 of struts 112 of collapsible valve frame fit underneath these retainers. The retaining members 140' therefore prevent collapsible frame 110 from disengaging from the base unit 100. Collapsible frame 110 is provided with a plurality of pivoting hooks 180, that rotate about a cylindrical portion of the top ends 136 of struts 112, as best shown in FIG. 28. This Figure shows a detailed view of the top end of a strut 112, showing a horizontal cylindrical portion 184 of the top end 136 of a strut 112. Cylindrical portion 184 joins a pair of adjacent struts 112. Two sets of articulation members 114 are provided at the top end 136 of a strut 112, rather than a single articulation member 114 that is present at the bottom end of a strut 112.

Figure 29A:
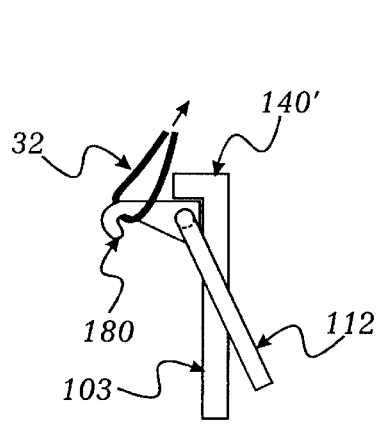
Figure 29B:
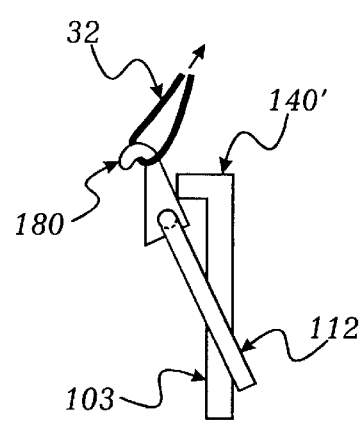
Figure 29C:
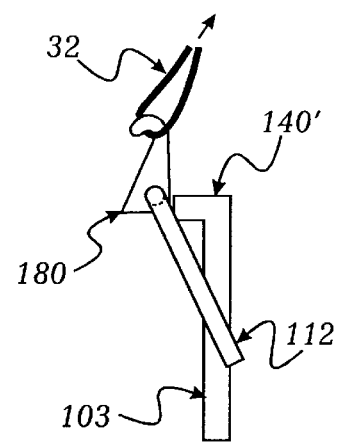
Figure 29D:
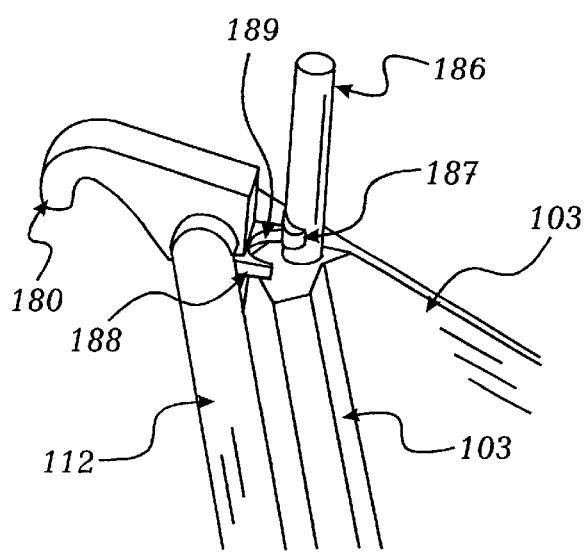
FIGS. 29D–29G illustrate the yet another alternative embodiment of engaging a collapsible valve to a base unit.

With reference to FIGS. 29A–29C, it can be seen that hooks 180 have a generally curved shape and project outward from collapsible frame 110, such that they can be captured by snares 32. Operation of hooks 180 will be described below.

Figure 29E:
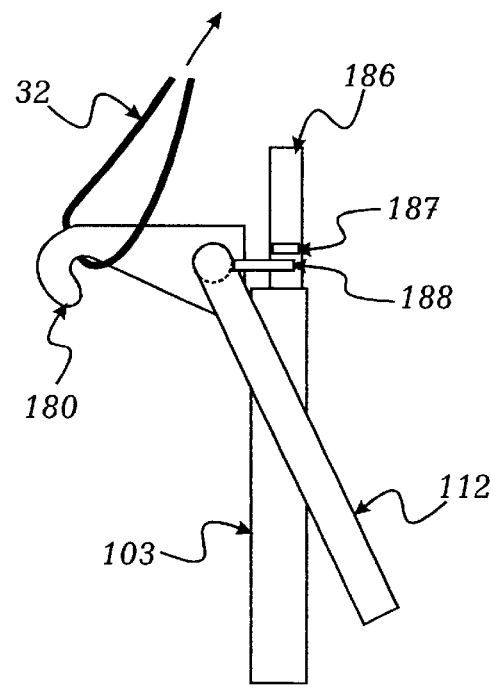
Figure 29F:
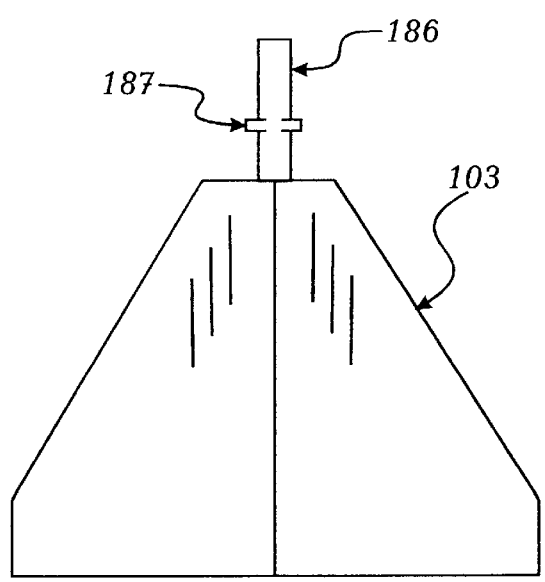
Figure 29G:
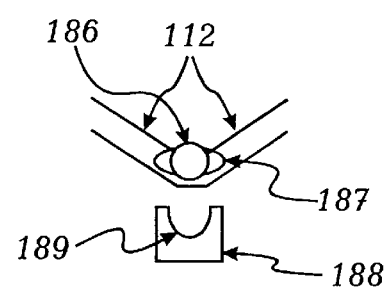

Referring now to FIG. 29D and FIGS. 29E–29G, there is shown yet another alternative embodiment of the cardiovascular valve system. Yet another means is used to retain collapsible frame 110 in engagement with permanent frame 102. FIGS. 29E, 29F and 29G respectively illustrate side, front and top views. In accordance with this embodiment of the cardiovascular valve system, struts 112 of collapsible frame 110 include a clip 188 that projects generally inward, towards the center of the valve and engages with post 186 that projects generally upward from top end of plates 103 of permanent frame 102. Clip 188 includes a recess or cut-out 189 that is dimensioned to receive post 186, to provide engagement therebetween. Post 186 also includes an enlarged portion or collar 187 having a largest dimension that is greater than the largest dimension of cut-out 189, thus inhibiting clip 188 from sliding upwards along post 186. This prevents collapsible valve 109 from disengaging from permanent frame 102. Collapsible valve 109 disengages from permanent frame 102 by deflection, caused by the action of hooks 180, as will be described below. Post 186 may also be suitably fitted with a hook at its end for capturing snares, if desired.

Figure 25A:
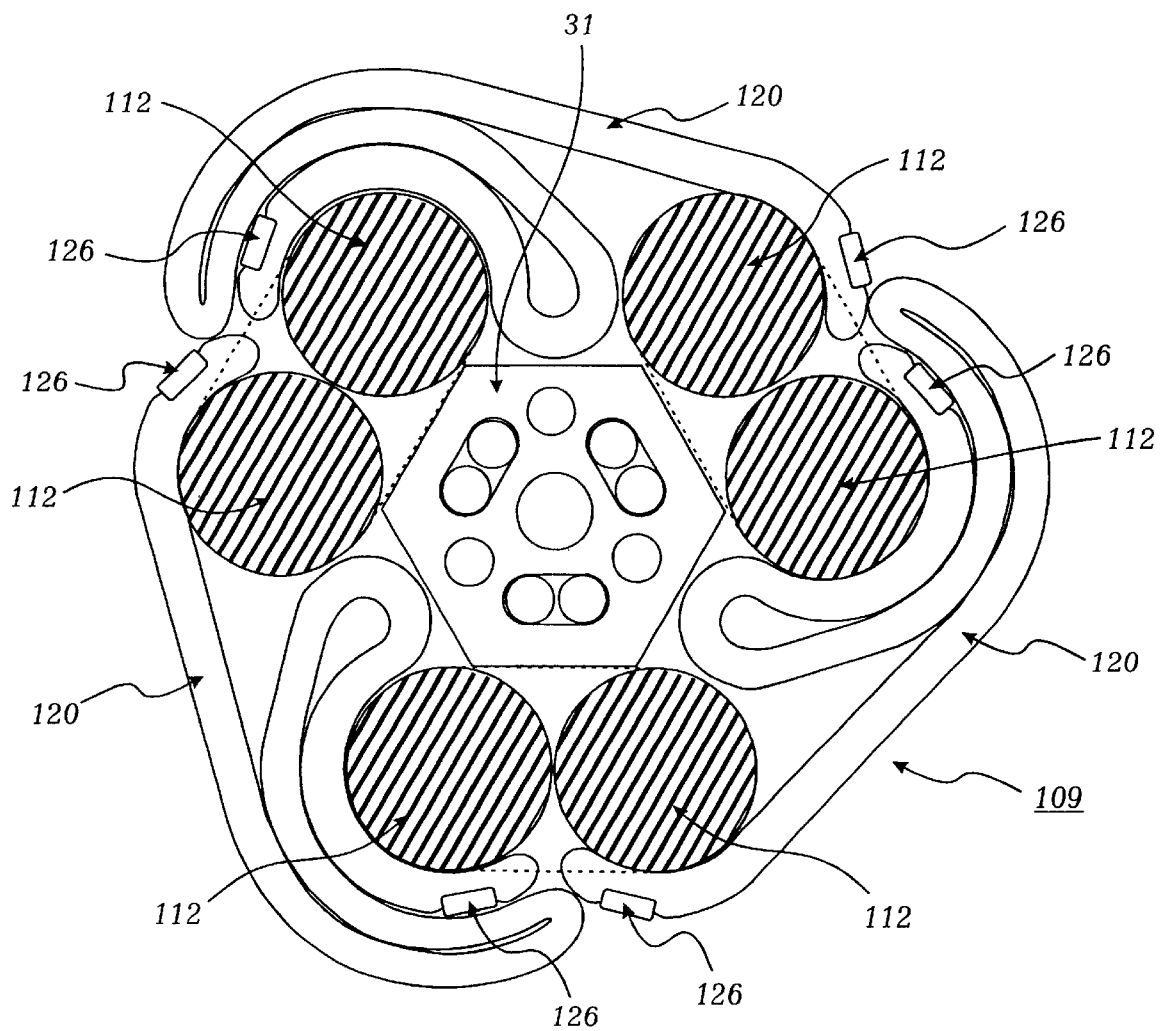
FIG. 25A shows a cross-sectional view of a collapsible valve fitted over a catheter body of a positioning catheter.

Referring now to FIG. 25A, there is shown a cross-sectional view of a collapsible valve 109 fitted over a distal catheter body 31 of a positioning catheter 33. As discussed above, a preferred embodiment of collapsible valve 109 includes a collapsible frame 110 having six rigid struts 112, to which three valve leaflets 120 are affixed. In the embodiment shown in FIG. 25A, the valve leaflets 120 are affixed to struts 112 by way of a strip of tacks 126.

Figure 25B:
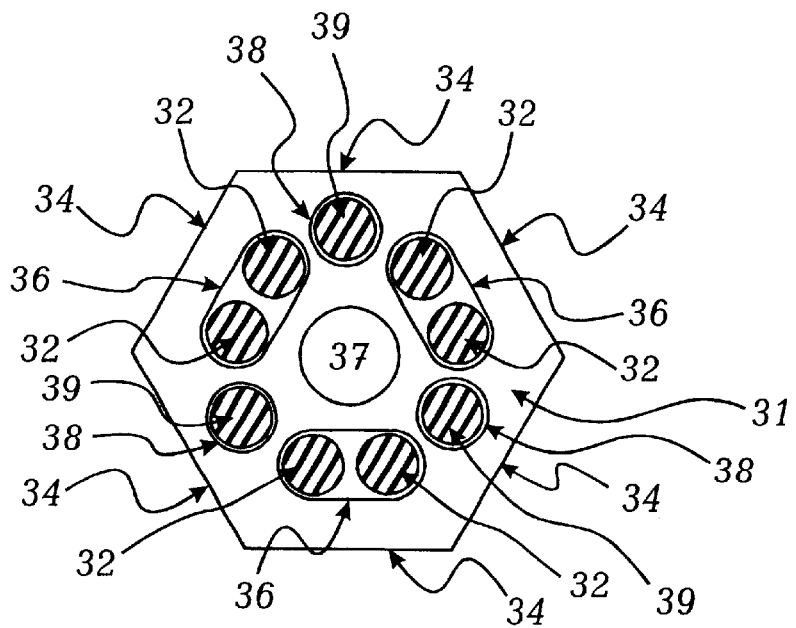
FIG. 25B shows a cross-sectional view of a catheter body of a positioning catheter.
Figure 25C:
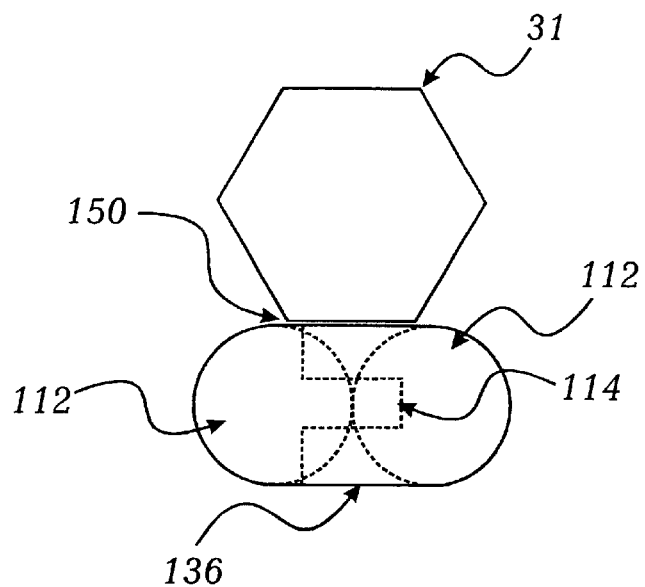
FIG. 25C illustrates a contact area for the outer surface of a catheter body and a portion of a collapsible valve.

FIG. 25B shows a cross-sectional view of a catheter body 31 of a positioning catheter 33, which is generally comprised of a generally circular polymer extrusion, (with a distal end that engages with the collapsible valve 109) has a number of flat facets 34. Facets 34 enable collapsible valve 109 to mate against the outer surface of catheter body 31. As shown in FIG. 25C, articulation member 114 at end 136 of struts 112 contacts with outer surface of catheter body 31 in a contact area 150. In accordance with a preferred embodiment, catheter body 31 has at least as many facets 34 as there are contact areas 150 between collapsible valve 109 and catheter body 31. It should be understood that the number of contact areas 150 is defined by the number and configuration of struts 112.

In accordance with a preferred embodiment of the present invention, catheter body 31 has a plurality of generally oval channels 36 and a plurality of generally round channels 38. Oval channels 36 are dimensioned to accommodate the loop of wire for the snares 32, while round channels 38 are dimensioned to accommodate pull wires to steer the catheter. A central lumen 37 may also be provided so as to enable catheter body 31 to be directed to the appropriate site by way of a guide wire.

Figure 30:
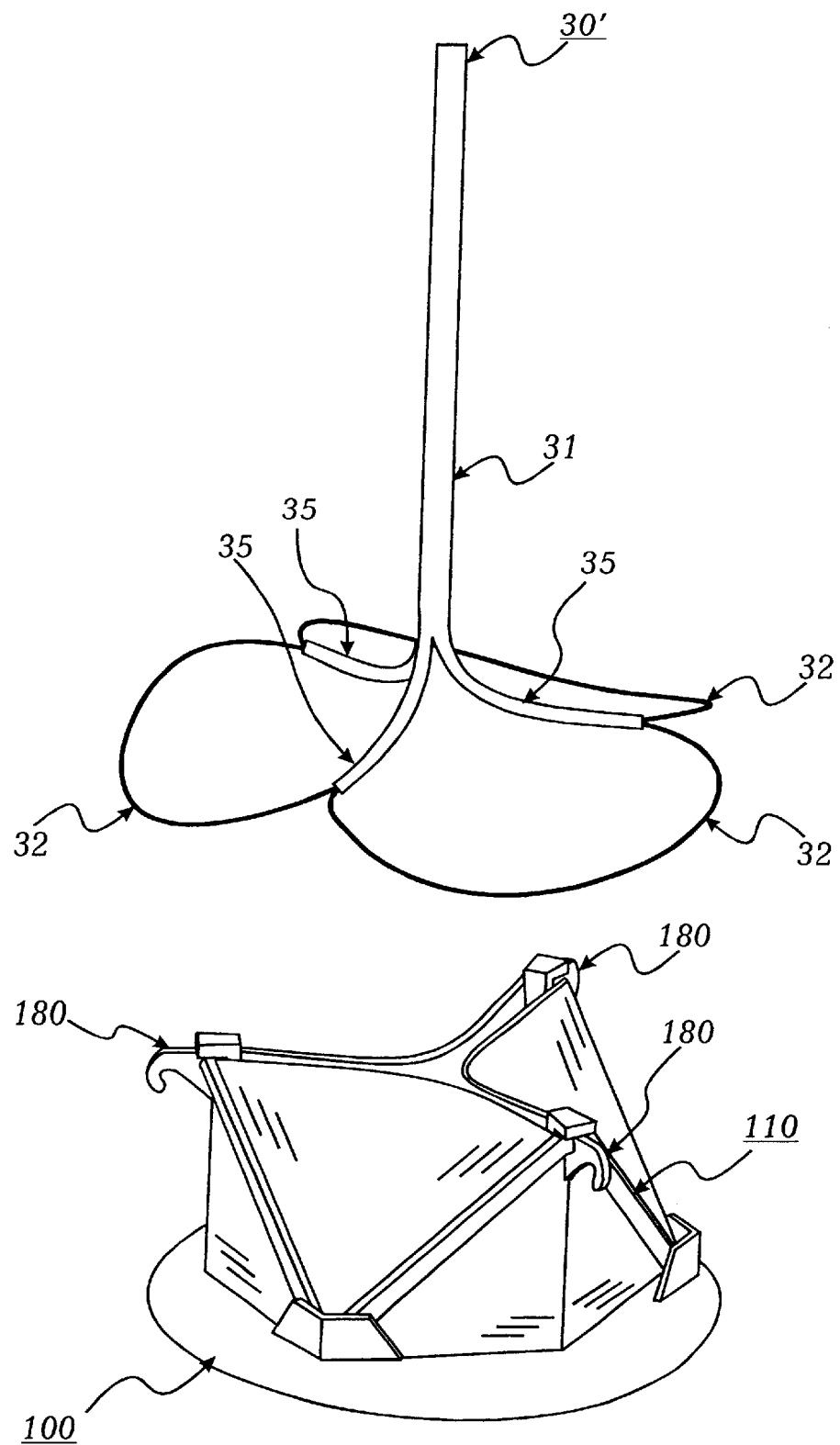
FIG. 30 illustrates use of a valve collapsing catheter in connection with the cardiovascular valve system of FIG. 27A.

Referring now to FIG. 30, there is shown an alternative embodiment of a valve collapsing catheter 30', including a catheter body 31 and preformed snares 32. In this embodiment, catheter body 31 is split into three segments 35. Snares 32 are fitted into each segment such that the two ends of snare 32 are drawn inward into different segments 35. This embodiment has the advantage of providing a nearly circular snare that can be more easily positioned over hooks 180 of collapsible frame 110.

II. Collapse and Expansion of the Collapsible Cardiac Valve

Figure 3A:
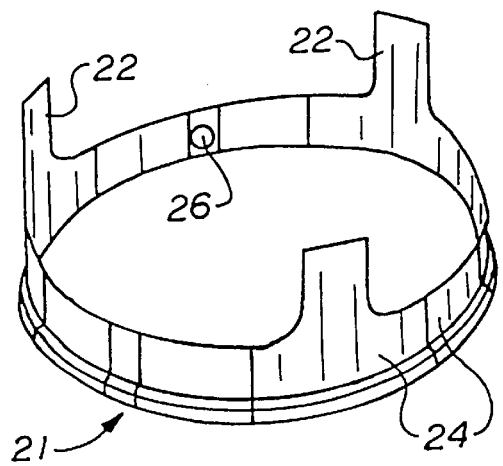
FIG. 3A shows a perspective view of the collapsible frame in accordance with a preferred embodiment of the present invention, in an expanded position.

During most of its useable life span, the collapsible valve 20 remains in its expanded state. The collapse of the inner frame 21 may be carried out with a remote manipulating device, such as valve collapsing catheter 30 (FIG. 6A) that includes one or more snares that grabs onto projections 26 or "handles" formed on the collapsible inner frame 21 (FIGS. 3A–3C). The valve collapsing catheter 30 includes a catheter body 31 and a plurality of cables preformed to conveniently sized loops or snare means 32. The snare means 32 can be extended from the catheter body 31 to preformed shapes, such that they can grab onto the projections 26 of the collapsible inner frame 21. When the snare means 32 are pulled back into the lumen of the catheter body 31, an inward force is achieved, sufficiently strong to "snap" the collapsible inner frame 21 into its collapsed position.

In the case of the alternative embodiment of the cardiovascular valve system described above with reference to FIGS. 10–30, the process of collapse may need to involve initial expansion, if collapsible frame 110 is configured as to be on the outside of plates 103, as shown in FIGS. 19B, 21 and 27–30. Since normal cardiac loads imposed on leaflets 120 of the closed valve are directed downwards and inwards, struts 112 of collapsible frame 110 are held tight against the outer surface of plates 103. Collapse of collapsible frame 110 therefore requires the top end 136 of struts 112 to be pushed outward during removal of collapsible frame 110 from permanent base unit 100. This prevents collapsible frame 110 from collapsing and disconnecting itself from plates 103 during normal valve function. The snap-in gussets 116 shown in FIGS. 20A and 20B are another such feature, in the case where collapsible frame 110 is configured to be positioned adjacent to the inner surface of plates 103, as shown in FIG. 19A.

Figure 6B:
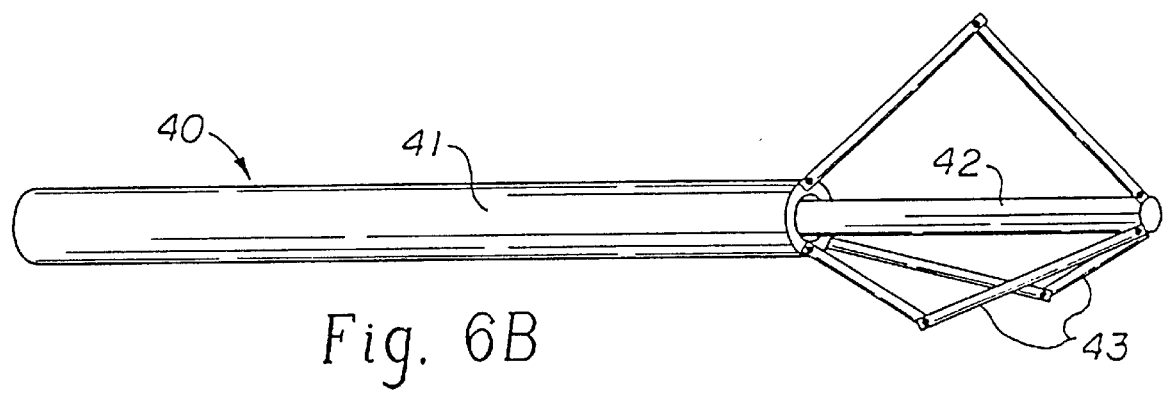
FIGS. 6B and 6C show an exemplary embodiment of a valve expanding catheter.
Figure 6C:
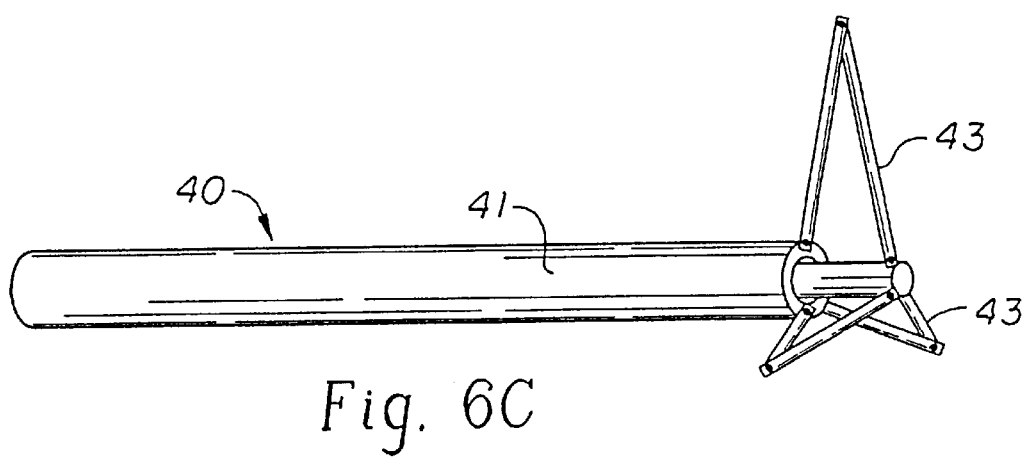
Figure 7E:
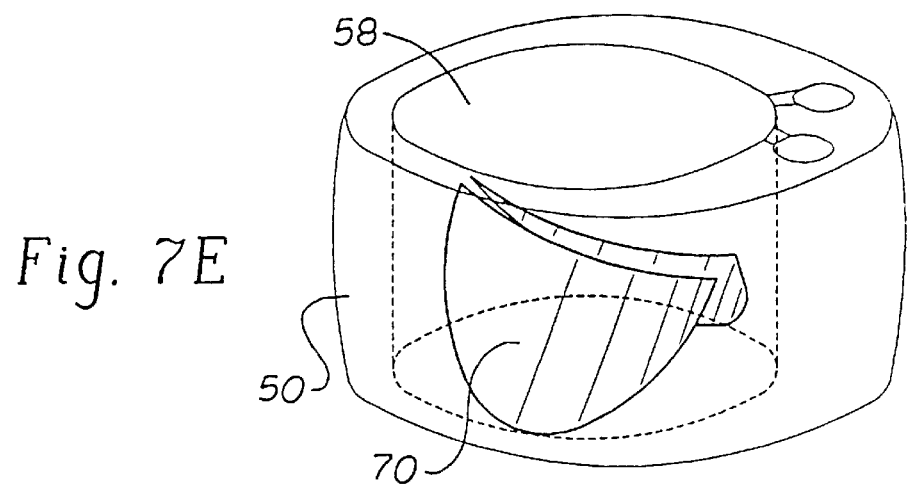
FIG. 7E illustrates a surgical platform having a check valve, in accordance with a preferred embodiment of the present invention.

The process of expansion of the inner frame 21 is opposite to the collapsing process. Referring now to FIGS. 6B and 6C, there is shown a suitable remote manipulating device for expanding the inner frame 21. Valve expanding catheter 40 includes a catheter body 41 and an articulating system 43 at its end that pushes against the projections 26 or some convenient segments 24 in order to expand the inner frame 21 and properly seat it in the outer frame 10. Valve expanding catheter 40 includes an inner rod 42 that slides in when pulled or pushed upon at its proximal end. Articulating system 43 is located at the distal end of inner rod 42, and includes a number of articulating arms or levers that hinge such that they expand when the inner rod 42 is drawn inwards. This action generates an outward push upon the inner frame 21 so that it expands and snaps into place in the rigid ring 11 of the outer frame 10. Because of the fit between the inner frame 21 and the rigid ring 11, the inner frame 21 cannot be separated from the outer frame 10 when expanded, and can only be separated when the inner frame 21 is in the collapsed position. Accordingly, the collapsible valve 20 safely operates when the inner frame 21 is in the expanded position.

Figures 26A, 26B:
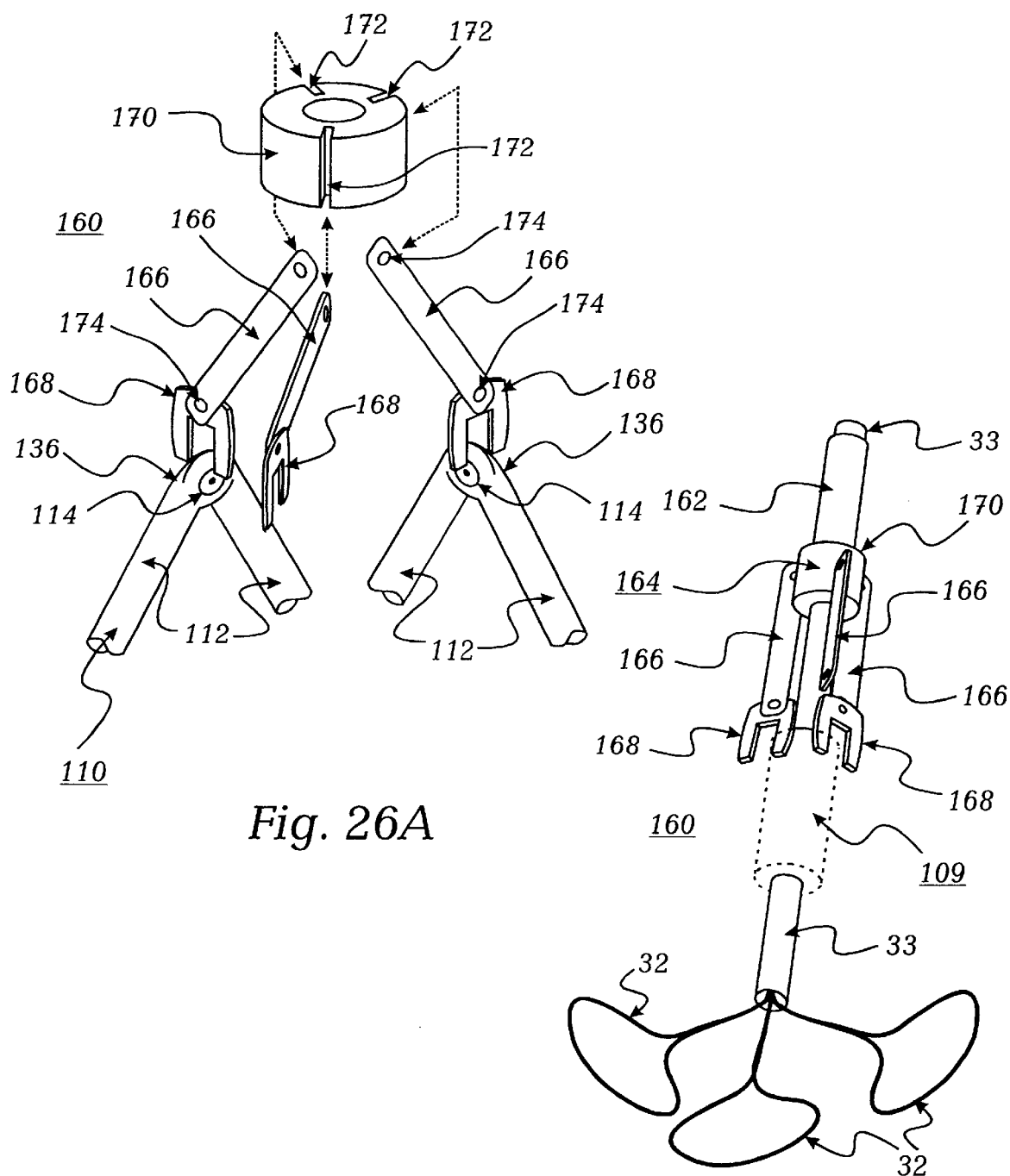
FIGS. 26A and 26B illustrate a valve expanding catheter 160.
Figure 26C:
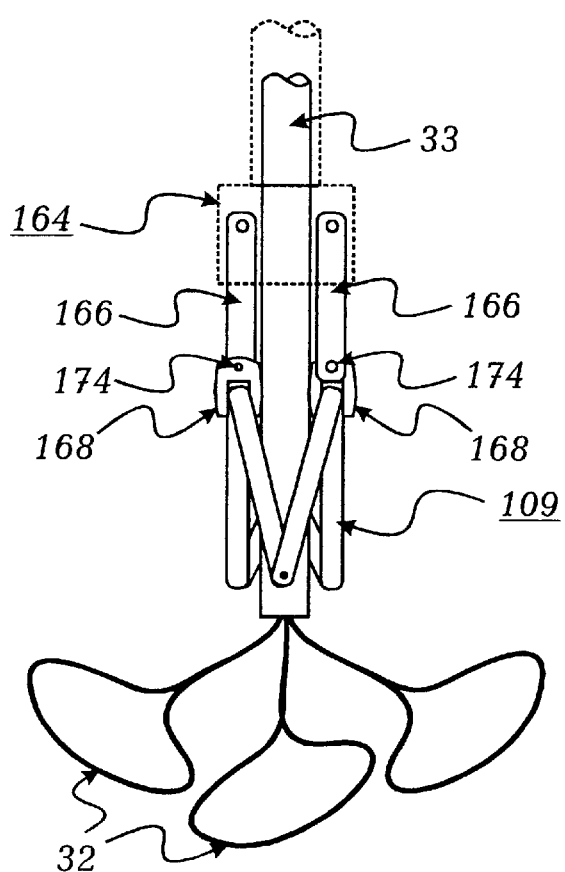
FIGS. 26C and 26D illustrate a procedure for expanding a collapsible valve for installation thereof, in accordance with the alternative embodiment shown in FIG. 22.

It should be understood that in the embodiments shown in FIGS. 10–25, the process of valve expansion and installation involves several co-axial catheters. Referring now to FIGS. 26A and 26B, there is shown a valve expanding catheter 160, which includes a catheter body 162 and a valve expander assembly 164 located at the distal end thereof. FIG. 26A provides a partially exploded view of valve expanding catheter 160. Valve expander assembly 164 includes a plurality of generally rigid legs 166. The distal end of each leg 166 is fitted with a strut clip 168 that can be snapped over the top of articulation member 114 at end 136 of struts 112 (FIG. 26A). The proximal end of each leg 166 is connected with a pusher ring 170, which is connected with a catheter body 162. 25 Legs 166 fit into pusher ring 170 by way of slots 172 that help stabilize articulating motion of valve expander assembly 164. In a preferred embodiment, strut clips 168 pivot about legs 166 by way of pin joints 174. Legs 166 pivot within pusher ring 170 by way of similar pin joints 174. Valve expanding catheter 160 fits over a positioning catheter 33, distal to a collapsed valve 109 (FIG. 26C).

Figure 26D:
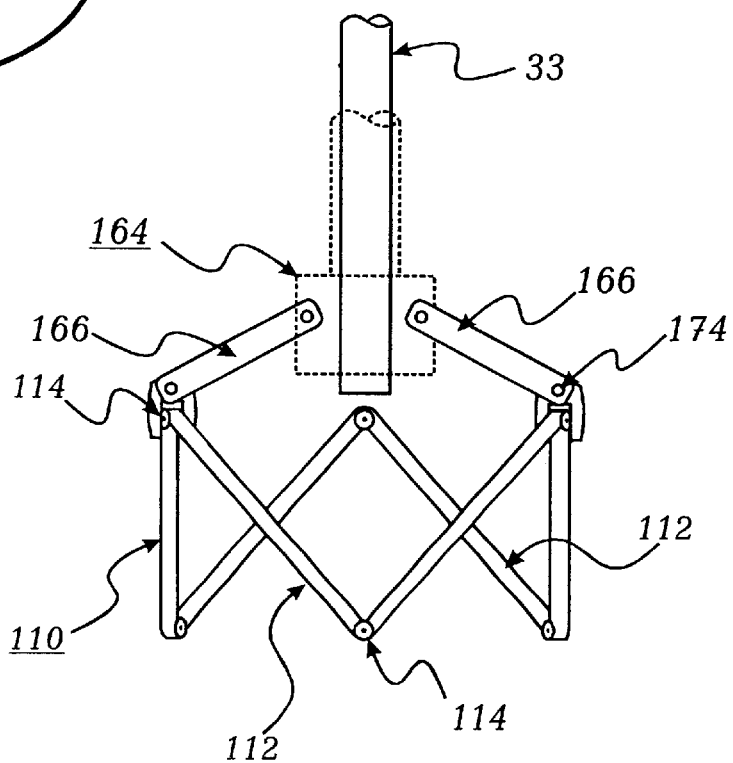

The process of expansion and installation of collapsible valve 109 will now be described in detail. First, notches 146 of projection portion 144 are snagged using snares 32 (FIG. 23C and 24). Snares 32 are then withdrawn into catheter body 31 (FIG. 24), which results in bending retaining clips 144 away from plates 103 (FIGS. 23C and 24). Next, valve expanding catheter 160 is pushed downward, causing collapsible valve 109 to impinge on taut snares 32 and expand. Consequently, legs 166 and strut clips 168 will pivot about pin joints 174 and articulate outward, as shown in FIGS. 26C and 26D. Once valve 109 has expanding such that its diameter is greater than that of permanent base unit 100, struts 112 will move downward into channels 117, best shown in FIG. 23. Once struts 112 have been received into channels 117, tension applied to snares 32 may be released, enabling projection portion 144 of retaining clips 140 to move back to their retain position (FIG. 23A). As a result, struts 112 are secured within channels 117. Expanding catheter 160 can then be withdrawn upwards, unsnapping strut clips 168 from struts 112, and thus releasing expanding catheter 160 from collapsible valve 109.

In the case of the alternative embodiment shown in FIG. 27A, FIGS. 29A–29C illustrate an exemplary method for disengaging collapsible frame 110 from base unit 100. Hooks 180 are rotatable between an engagement position (FIG. 29A) and a disengagement position. With regard to disengagement, when the snares 32 are pulled upward back into a catheter 31(see FIG. 6A), hooks 180 rotate and act as a lever to deflect the top ends 136 of struts 112 outward (i.e., away from base unit 100), thus expanding collapsible frame 110. Consequently, the top ends 136 of the collapsible frame 110 move past retaining members 140', resulting in the disengagement of collapsible frame 110 from base unit 100.

In the case of the alternative embodiment shown in FIGS. 29D–29G, rotation of hooks 180 acts to deflect top ends 136 of struts 112 outward (i.e., away from base unit 100), thus expanding collapsible frame 110. Consequently, clip 188 moves past collar 187, resulting in the disengagement of collapsible frame 110 from base unit 100.

III. Intra Cardiac Removal and Delivery of Collapsible Cardiac Valve

The system for collapse, removal and delivery of a replacement collapsible valve makes use of novel catheter technologies. A catheter-based valve delivery system must itself be collapsible so that it can be inserted percutaneously, and deliverable by catheter to the appropriate site. In accordance with a preferred embodiment of the present invention, a catheter-based valve delivery system is generally comprised of several catheters or catheter sheaths, that can shuttle components in and out of the body to the desired spot with minimal repositioning.

FIGS. 7A–7E illustrate components of a delivery system, according to a preferred embodiment of the present invention. The distal end of the delivery system is anchored in the ascending aorta, and is referred to herein as the surgical platform 50. All catheters C1, 53 and 57, and other valve manipulation devices have their distal ends anchored within the surgical platform 50, so that they can be stable at their distal end and perform their function with good control and accuracy. The catheters, themselves act as remote manipulators that can be controlled by pull wires, or by means of small actuators controlled electrically or hydraulically that deflect the catheters or in some way change their shape. Since the objectives of some of the catheters is to deliver the collapsible valve 20 and other components from the outside of the patient to the operative site inside the patient, these catheters have an inner lumen through which pull cables and other catheters can slide.

The shuttling of larger objects between the outside world and the surgical platform 50 is achieved by splitting the main guiding catheter 53 along its length to form an elongated slot 55. Accordingly, main guiding catheter 53 acts as a slotted catheter sheath for inner pull cables or an inner catheter 57. Inner catheter 57 has gripping means 54 that project through slot 55 spanning the wall of the main guiding catheter 53. Gripping means 54 attach collapsible valve 20 or other devices to inner catheter 57, and slide along slot 55, as will be explained in detail below. Accordingly, the slotted main guiding catheter 53 and inner catheter 57 provide a "monorail" system that conveniently transports devices in and out of the body by moving them along the length of the main guiding catheter 53.

Since the collapsible valve 20 and other devices may not fit inside a typical catheter, they must be delivered to the operative site along the outside of the main guiding catheter 53. Moreover, the collapsible valve 20 needs to be passed through the surgical platform 50 to the operative site, the slots 55 need to be continuous through the surgical platform 50. Accordingly, the surgical platform 50 is fitted with appropriate similar slots 56 so that the surgical platform 50 does not interfere with the passage of objects along the main guiding catheter 53.

The main guiding catheter 53 is locked in place to the surgical platform 50 by means of a system, such as a twist or snap connector, that lines up the slot 55 of the main guiding catheter 53 with the slot 56 formed in the surgical platform 50. Objects that are passed through the vasculature to the operative site, can be anchored to the inner catheter 57. In this regard, gripping means 54 may include a simple, spring-loaded clamp 59 that is held closed by a conventional coil spring 51 (FIG. 7D). The spring 51 can be opened remotely simply by pushing the inner catheter 57 against the closed end 75 of the main guiding catheter 53. This generates a pushing force on the clamp 59 and allows one of the jaws to rotate, thus opening the clamp and releasing the device. It will be appreciated that gripping means 54 may take other suitable forms.

Figure 8A:
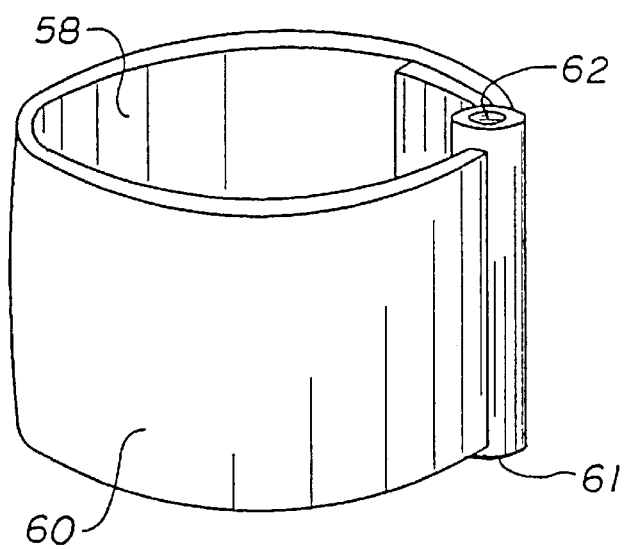
FIG. 8A shows an alternative embodiment of an expandable surgical platform.
Figure 8B:
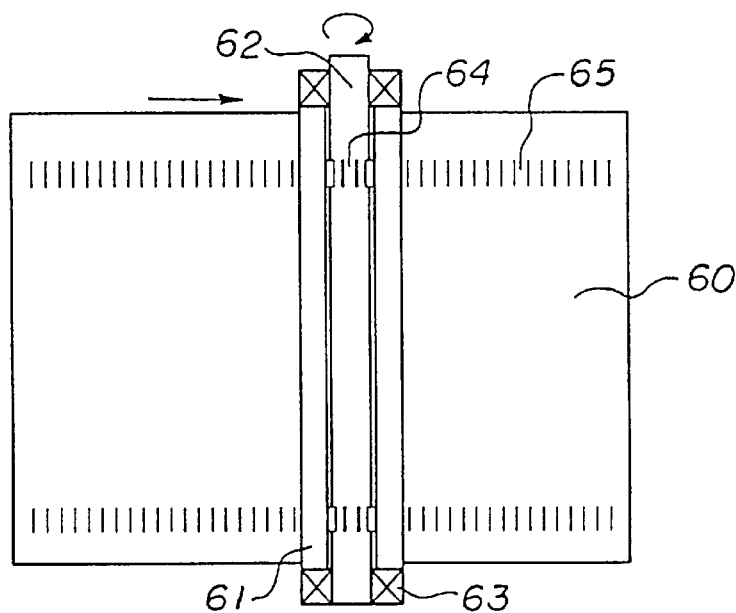
FIG. 8B is a schematic representation illustrating operation of the expandable surgical platform shown in FIG. 8A.

The surgical platform 50 can be fabricated from balloon technology, as shown in FIG. 7A. Alternatively, as shown in FIGS. 8A and 8B, a cylindrical surgical platform 60 can be formed from a wound strip of material that is held in a fitting 61 and unrolls by means of a rotating shaft 62. This means of unwrapping or expanding the wound strip of material to increase its diameter structure, operates in a manner similar to the way that a "hose clamp" reduces its diameter, when being wound up. The rotating shaft 62 can sit suspended within the fitting 61 by means of bushings 63. The shaft 62 can deliver its torque to the wound strip of material through a friction contact, or by means of short teeth or textured bumps 64, that engage with similar depression, pits, or slots 65 on the inner surface of the wound strip of material.

It should be appreciated that the delivery system, and in particular the surgical platforms 50, 60 may also contain an auxiliary synthetic check valve 70 (FIG. 7E) that cyclically opens and closes, replacing the function of the worn out collapsible valve while it is being removed and replaced with a new collapsible valve. The synthetic check valve 70 may be integrated into the lumen 58 of the surgical platform 50. The synthetic check valve 70 is comprised of a one or more flaps of polymer that seal the lumen 58 when the check valve 70 is closed, and move out of the way when the check valve 70 opens passively as blood is ejected from the heart. There is provision made for manually opening the check valve 70 by means of catheters and pull wires, so that larger objects can be passed by this check valve on the way to the operative site. Alternatively, the action of the one-way check valve 70 can be replaced by an occluding balloon that cyclically expands and collapses under external control, and occludes the aorta distal to the surgical platform.

Figure 31A:
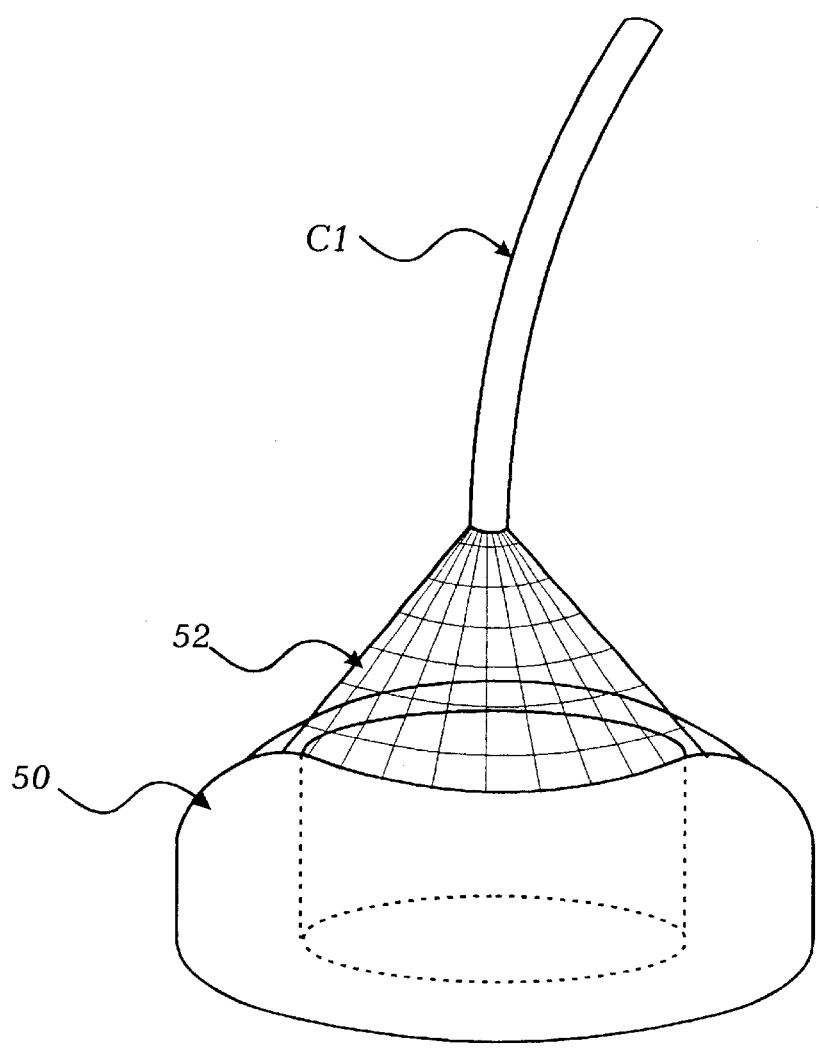
FIGS. 31A and 31B illustrate a surgical platform according to an alternative embodiment of the present invention, wherein a screen is incorporated to trap particulates (FIG. 31A), and a synthetic valve is incorporated to control the flow of blood (FIG. 31B).
Figure 31B:
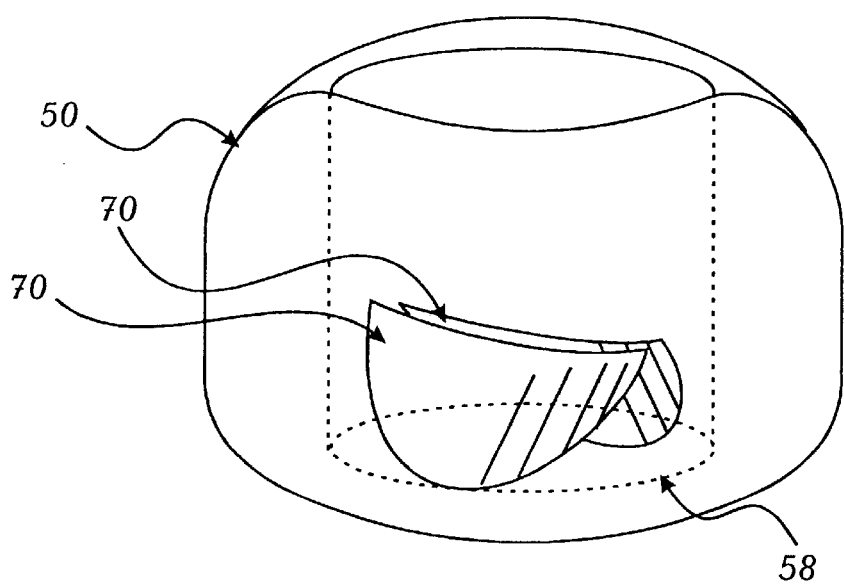

In an alternative embodiment of surgical platform 50, a sieve or a screen 52 is provided that enshrouds the lumen 58 of the surgical platform (FIG. 31A). This sieve can be delivered in a collapsed, or rolled up state within the deliver catheter Cl, and automatically deployed as the surgical platform is expanded. In the case where the sieve is not fitted with an integral check valve, it can be used as a sheath to cover the collapsed valve during withdrawal from the patient, thus preventing scratching of the vasculature on its way out.

IV. Imaging System for Implantation of Collapsible Cardiac Valve

Complex, remote surgery such as described above, requires a suitable device tracking and visualization system. Most MIS procedures are performed on organs that do not involve considerable bleeding since the surgeon is oriented and guided only with his own vision, using endoscopic video cameras. Using endoscopes in a bloody environment is not convenient because blood is opaque. Optical visualization and localization inside the beating heart is simply impractical.

Such a system will therefore need real-time, high resolution ultrasound imaging, continuous X-ray fluoroscopy, or some combination of both. Real-time open magnet MRI is also an option, but the need for high strength metallic instruments in this system makes MRI unlikely. X-ray imaging is undesirable because of the harmful radiation, and ultrasound does not currently have sufficient spatial resolution when operated in 3-D mode and is unlikely to in the near future. Ultrasound imaging is also susceptible to shadowing from dense, metallic objects. Innovative imaging modalities alone, may not be sufficient for properly guiding the valve replacement procedure. A 3-D visualization system, that integrates multiple imaging modalities and real time device tracking, is therefore most suitable. For instance, an ultrasonic catheter and device tracking system, analogous to that described in U.S. Pat. No. 5,515,853 (incorporated herein by reference), would be very appropriate, if linked to a powerful 3-D graphics engine that can simulate the position and movement of the various objects as they are manipulated inside the patient. Another device tracking system that could be used would employ electromagnetic localizer technology, such as that described in U.S. Pat. No. 5,546,951 (incorporated herein by reference). Other electrical, magnetic or image based localizer system can be used with similar function. To provide additional information, numerous images obtained simultaneously using ultrasound, X-ray or other imaging modalities could be integrated into this viewing environment, as described in U.S. Pat. No. 5,817,022 (incorporated herein by reference), to provide additional feedback regarding the true position of the objects. The imaging heads for any optical, acoustic, radiographic or electromagnetic imaging systems can be incorporated into the surgical platform for monitoring of the valve replacement procedure.

V. Other Uses of Device Delivery System

There is a growing number of surgical and therapeutic procedures that involve the delivery of a device or multiple devices to the inside of a body to a site of surgery or device deployment. To date, all of these systems employed a conventional catheter without the longitudinal split, and without the use of a surgical platform. Use of the present invention: (i) enables the delivery of larger devices to the target site by the use of smaller catheters, and (ii) stabilizes the distal end of the catheter for much more precise, more controllable catheter-based procedures. Such a surgical platform can be used for ablation procedures within the ventricles and the atria by better stabilizing the catheters, for the delivery of larger endovascular prostheses or occluding devices to stop internal bleeding, such as in cirrhotic liver vessels or ventricular-septal defects. The surgical platforms for such applications do not need to incorporate internal valves and can therefore be simplified into baskets or cages or articulating structures that simply lodge themselves against the appropriate anatomy, as shown in FIGS. 9A–9C, in the case for atrial access. In this embodiment, the surgical platform 80 includes forked projections 81 that slide out of a main catheter 82 and lodge themselves against appropriate cardiac anatomy, such as the commissures of the mitral valve 85. The "commissure" is an anatomic site, defined as the spot where the anterior leaflet 86 meets the posterior leaflet 87. These commissures are also located between the atrium 88 and the ventricle 89, which in themselves provide walls or surfaces against which the projections 81 can be anchored.

The present invention has been described with reference to a preferred embodiment. Obviously, it will be appreciated by those skilled in the art that various additions, modifications, deletions and alterations will occur to others upon a reading and understanding of this specification, and may be made to such preferred embodiments without departing from the spirit and scope of the invention. Accordingly, it is intended that all such modifications and alterations be included within the scope of the invention as defined in the following claims.

Having thus described the invention, it is now claimed:

1. A cardiovascular valve system comprising:
   a base unit permanently attachable to tissue; and
   a collapsible valve engageable and disengageable with said base unit, wherein said collapsible valve includes a collapsible frame having a plurality of articulated struts, said collapsible frame movable between an expanded position to engage the collapsible valve with the base unit, and a collapsed position to disengage the collapsible valve from the base unit.

2. A cardiovascular valve system according to claim 1, wherein collapsible valve further includes an occluding member movable between an occluded position and an open position, said occluding member supported by said collapsible frame.

3. A cardiovascular valve system according to claim 2, wherein said occluding member includes at least one leaflet occluder.

4. A cardiovascular valve system according to claim 1, wherein said articulated struts are generally rigid.

5. A cardiovascular valve system according to claim 1, wherein said base unit includes a receptacle for receiving the collapsible valve.

6. A cardiovascular valve system according to claim 5, wherein said receptacle includes a plurality of plates.

7. A cardiovascular valve system according to claim 1, wherein said system further comprises at least one retaining member for retaining the engagement of said collapsible valve with said permanent base unit.

8. A cardiovascular valve system according to claim 7, wherein said retaining member includes a gusset.

9. A cardiovascular valve system according to claim 7, wherein said retaining member includes a slot.

10. A cardiovascular valve system according to claim 7, wherein said retaining member includes a generally elastic retaining clip.

11. A cardiovascular valve system according to claim 7, wherein said retaining member includes a channel.

12. A cardiovascular valve system according to claim 7, wherein said retaining member includes a generally rigid retainer.

13. A cardiovascular valve system according to claim 7, wherein said collapsible frame includes articulating hook members, said articulating hook members engageable with said retaining member.

14. A cardiovascular valve system according to claim 13, wherein said articulating hook members are rotatable between an engagement position and a disengagement position.

15. A cardiovascular valve system comprising:

a base unit permanently attachable to tissue, said base unit including a receptacle; and a collapsible valve engageable and disengageable with the receptacle, wherein said collapsible valve includes a collapsible frame having a plurality of articulated struts, said collapsible frame movable between an expanded position to engage the collapsible valve with the receptacle, and a collapsed position to disengage the collapsible valve from the receptacle.

16. A cardiovascular valve system according to claim 15, wherein said receptacle includes a plurality of plates.

17. A cardiovascular valve system according to claim 16, wherein said plurality of plates are generally triangular.

18. A cardiovascular valve system according to claim 17, wherein said plurality of plates form a valve orifice.

19. A cardiovascular valve system according to claim 15, wherein said collapsible valve includes at least one leaflet attached with said plurality of articulated struts.

20. A cardiovascular valve system according to claim 15, wherein said collapsible frame includes articulating hook members, said articulating hook members engageable with said base unit.

* * * * *